US010265526B2

(12) United States Patent
Khalil et al.

(10) Patent No.: US 10,265,526 B2
(45) Date of Patent: *Apr. 23, 2019

(54) SPINAL CORD STIMULATOR SYSTEM

(71) Applicant: CIRTEC MEDICAL CORP., Brooklyn Park, MN (US)

(72) Inventors: Saif Khalil, Wayne, PA (US); Raghavendra Angara, West Chester, PA (US); Miles Curtis, Philadelphia, PA (US); Christopher Biele, King of Prussia, PA (US); Daniel Fellmeth, Eagleville, PA (US)

(73) Assignee: Cirtec Medical Corp., Brooklyn Park, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/003,275

(22) Filed: Jun. 8, 2018

(65) Prior Publication Data

US 2018/0289963 A1  Oct. 11, 2018

Related U.S. Application Data

(63) Continuation of application No. 14/213,266, filed on Mar. 14, 2014, now Pat. No. 10,016,602.
(Continued)

(51) Int. Cl.
*A61N 1/36* (2006.01)
*A61N 1/372* (2006.01)
(Continued)

(52) U.S. Cl.
CPC ......... *A61N 1/36071* (2013.01); *A61N 1/025* (2013.01); *A61N 1/0551* (2013.01);
(Continued)

(58) Field of Classification Search
CPC .......................... A61N 1/37223; A61N 1/3787
See application file for complete search history.

(56) References Cited

U.S. PATENT DOCUMENTS

| 3,195,540 A | 7/1965 | Waller |
| 3,718,134 A | 2/1973 | Brindley |
(Continued)

FOREIGN PATENT DOCUMENTS

WO      0209808 A1    2/2002

*Primary Examiner* — George R Evanisko
(74) *Attorney, Agent, or Firm* — Craig J. Lervick; Larkin Hoffman Daly & Lindgren, Ltd.

(57) ABSTRACT

Spinal cord stimulation (SCS) system having a recharging system with self alignment, a system for mapping current fields using a completely wireless system, multiple independent electrode stimulation outsource, and control through software on Smartphone/mobile device and tablet hardware during trial and permanent implants. SCS system can include multiple electrodes, multiple, independently programmable, stimulation channels within an implantable pulse generator (IPG) providing concurrent, but unique stimulation fields. SCS system can include a replenishable power source, rechargeable using transcutaneous power transmissions between antenna coil pairs. An external charger unit, having its own rechargeable battery, can charge the IPG replenishable power source. A real-time clock can provide an auto-run schedule for daily stimulation. A bi-directional telemetry link informs the patient or clinician the status of the system, including the state of charge of the IPG battery. Other processing circuitry in current IPG allows electrode impedance measurements to be made.

20 Claims, 11 Drawing Sheets

Related U.S. Application Data

(60) Provisional application No. 61/792,654, filed on Mar. 15, 2013.

(51) Int. Cl.
*A61N 1/378* (2006.01)
*A61N 1/375* (2006.01)
*A61N 1/02* (2006.01)
*A61N 1/05* (2006.01)

(52) U.S. Cl.
CPC ....... *A61N 1/0553* (2013.01); *A61N 1/36125* (2013.01); *A61N 1/36157* (2013.01); *A61N 1/36178* (2013.01); *A61N 1/36185* (2013.01); *A61N 1/3752* (2013.01); *A61N 1/3754* (2013.01); *A61N 1/3787* (2013.01); *A61N 1/37217* (2013.01); *A61N 1/37223* (2013.01); *A61N 1/37229* (2013.01); *A61N 1/37235* (2013.01); *A61N 1/37241* (2013.01)

(56) References Cited

U.S. PATENT DOCUMENTS

| | | | |
|---|---|---|---|
| 3,724,467 | A | 4/1973 | Avery et al. |
| 3,727,616 | A | 4/1973 | Lenzkes |
| 3,822,708 | A | 7/1974 | Zilber |
| 3,867,950 | A | 2/1975 | Fischell |
| 3,888,260 | A | 6/1975 | Fischell |
| 3,942,535 | A | 3/1976 | Schulman |
| 4,014,346 | A | 3/1977 | Brownlee et al. |
| 4,019,518 | A | 4/1977 | Maurer et al. |
| 4,082,097 | A | 4/1978 | Mann et al. |
| 4,134,408 | A | 1/1979 | Brownlee et al. |
| 4,232,679 | A | 11/1980 | Schulman |
| 4,379,462 | A | 4/1983 | Borkan et al. |
| 4,390,023 | A | 6/1983 | Rise |
| 4,408,608 | A | 10/1983 | Daly et al. |
| 4,459,989 | A | 7/1984 | Borkan |
| 4,510,936 | A | 4/1985 | Fourcin et al. |
| 4,512,351 | A | 4/1985 | Pohndorf |
| 4,541,432 | A | 9/1985 | Molina-Negro et al. |
| 4,549,556 | A | 10/1985 | Tarjan et al. |
| 4,608,986 | A | 9/1986 | Beranek et al. |
| 4,640,286 | A | 2/1987 | Thomson |
| 4,690,145 | A | 9/1987 | King-Smith et al. |
| 4,712,558 | A | 12/1987 | Kidd et al. |
| 5,036,850 | A | 8/1991 | Owens |
| 5,119,832 | A | 6/1992 | Xavier |
| 5,143,067 | A | 9/1992 | Rise et al. |
| 5,255,691 | A | 10/1993 | Otten |
| 5,279,292 | A | 1/1994 | Baumann et al. |
| 5,314,457 | A | 5/1994 | Jeutter et al. |
| 5,354,320 | A | 10/1994 | Schaldach et al. |
| 5,374,285 | A | 12/1994 | Vaiani et al. |
| 5,391,193 | A | 2/1995 | Thompson |
| 5,411,537 | A | 5/1995 | Munshi et al. |
| 5,417,719 | A | 5/1995 | Hull et al. |
| 5,441,527 | A | 8/1995 | Erickson et al. |
| 5,443,486 | A | 8/1995 | Hrdlicka et al. |
| 5,458,629 | A | 10/1995 | Baudino et al. |
| 5,458,631 | A | 10/1995 | Xavier |
| 5,501,703 | A | 3/1996 | Holsheimer et al. |
| 5,591,217 | A | 1/1997 | Barreras |
| 5,630,835 | A | 5/1997 | Brownlee |
| 5,643,330 | A | 7/1997 | Holsheimer et al. |
| 5,662,689 | A | 9/1997 | Elsberry et al. |
| 5,690,693 | A | 11/1997 | Wang et al. |
| 5,702,431 | A | 12/1997 | Wang et al. |
| 5,713,939 | A | 2/1998 | Nedungadi et al. |
| 5,733,313 | A | 3/1998 | Barreras et al. |
| 5,733,322 | A | 3/1998 | Starkebaum |
| 5,769,877 | A | 6/1998 | Barreras, Sr. |
| 5,843,146 | A | 12/1998 | Cross, Jr. |
| 5,861,019 | A | 1/1999 | Sun et al. |
| 5,865,843 | A | 2/1999 | Baudino |
| 5,893,883 | A | 4/1999 | Torgerson et al. |
| 5,895,416 | A | 4/1999 | Barreras et al. |
| 5,913,882 | A | 6/1999 | King |
| 5,935,159 | A | 8/1999 | Cross, Jr. et al. |
| 5,938,690 | A | 8/1999 | Law et al. |
| 6,009,350 | A | 12/1999 | Renken |
| 6,052,623 | A | 4/2000 | Fenner et al. |
| 6,052,624 | A | 4/2000 | Mann |
| 6,066,165 | A | 5/2000 | Racz |
| 6,120,502 | A | 9/2000 | Michelson |
| 6,167,312 | A | 12/2000 | Goedeke |
| 6,169,925 | B1 | 1/2001 | Villaseca et al. |
| 6,175,769 | B1 | 1/2001 | Errico et al. |
| 6,181,969 | B1 | 1/2001 | Gord |
| 6,181,971 | B1 | 1/2001 | Doan |
| 6,185,452 | B1 | 2/2001 | Schulman et al. |
| 6,185,463 | B1 | 2/2001 | Baudino |
| 6,205,361 | B1 | 3/2001 | Kuzma et al. |
| 6,208,894 | B1 | 3/2001 | Schulman et al. |
| 6,216,045 | B1 | 4/2001 | Black et al. |
| 6,227,204 | B1 | 5/2001 | Baumann et al. |
| 6,236,892 | B1 | 5/2001 | Feler |
| 6,240,317 | B1 | 5/2001 | Villaseca et al. |
| 6,240,318 | B1 | 5/2001 | Philips |
| 6,246,912 | B1 | 6/2001 | Sluijter et al. |
| 6,249,705 | B1 | 6/2001 | Snell |
| 6,249,707 | B1 | 6/2001 | Kohnen et al. |
| 6,266,564 | B1 | 7/2001 | Hill et al. |
| 6,309,401 | B1 | 10/2001 | Redko et al. |
| 6,379,300 | B1 | 4/2002 | Haubrich |
| 6,381,496 | B1 | 4/2002 | Meadows et al. |
| 6,393,325 | B1 | 5/2002 | Mann et al. |
| 6,415,187 | B1 | 7/2002 | Kuzma et al. |
| 6,456,256 | B1 | 9/2002 | Amundson et al. |
| 6,456,887 | B1 | 9/2002 | Dudding et al. |
| 6,463,329 | B1 | 10/2002 | Goedeke |
| 6,473,653 | B1 | 10/2002 | Schallhorn et al. |
| 6,477,424 | B1 | 11/2002 | Thompson et al. |
| 6,505,072 | B1 | 1/2003 | Linder et al. |
| 6,505,401 | B1 | 1/2003 | Doan |
| 6,516,227 | B1 | 2/2003 | Meadows et al. |
| 6,522,932 | B1 | 2/2003 | Kuzma et al. |
| 6,535,766 | B1 | 3/2003 | Thompson et al. |
| 6,539,253 | B2 | 3/2003 | Thompson et al. |
| 6,553,263 | B1 | 4/2003 | Meadows et al. |
| 6,553,264 | B2 | 4/2003 | Redko et al. |
| 6,587,724 | B2 | 7/2003 | Mann |
| 6,600,954 | B2 | 7/2003 | Cohen et al. |
| 6,609,031 | B1 | 8/2003 | Law et al. |
| 6,609,032 | B1 | 8/2003 | Woods et al. |
| 6,614,406 | B2 | 9/2003 | Amundson et al. |
| 6,622,048 | B1 | 9/2003 | Mann et al. |
| 6,650,944 | B2 | 11/2003 | Goedeke et al. |
| 6,654,642 | B2 | 11/2003 | Boydston et al. |
| 6,658,297 | B2 | 12/2003 | Loeb |
| 6,658,302 | B1 | 12/2003 | Kuzma et al. |
| 6,662,052 | B1 | 12/2003 | Sarwal et al. |
| 6,662,053 | B2 | 12/2003 | Borkan |
| 6,664,763 | B2 | 12/2003 | Echarri et al. |
| 6,671,544 | B2 | 12/2003 | Baudino |
| 6,675,045 | B2 | 1/2004 | Mass et al. |
| 6,675,046 | B2 | 1/2004 | Holsheimer |
| 6,708,065 | B2 | 3/2004 | Von Arx et al. |
| 6,741,892 | B1 | 5/2004 | Meadows et al. |
| 6,745,079 | B2 | 6/2004 | King |
| 6,757,970 | B1 | 7/2004 | Kuzma et al. |
| 6,795,737 | B2 | 9/2004 | Gielen et al. |
| 6,809,701 | B2 | 10/2004 | Amundson et al. |
| RE38,654 | E | 11/2004 | Hill et al. |
| 6,819,958 | B2 | 11/2004 | Weiner et al. |
| 6,847,849 | B2 | 1/2005 | Mamo et al. |
| 6,850,802 | B2 | 2/2005 | Holsheimer |
| 6,868,288 | B2 | 3/2005 | Thompson |
| 6,871,099 | B1 | 3/2005 | Whitehurst et al. |
| 6,889,086 | B2 | 5/2005 | Mass et al. |
| 6,892,097 | B2 | 5/2005 | Holsheimer |
| 6,895,280 | B2 | 5/2005 | Meadows et al. |
| 6,895,283 | B2 | 5/2005 | Erickson et al. |

(56) References Cited

U.S. PATENT DOCUMENTS

| | | |
|---|---|---|
| 6,901,292 B2 | 5/2005 | Hrdlicka et al. |
| 6,909,917 B2 | 6/2005 | Woods et al. |
| 6,920,359 B2 | 7/2005 | Meadows et al. |
| 6,930,602 B2 | 8/2005 | Dublin et al. |
| 6,937,891 B2 | 8/2005 | Leinders et al. |
| 6,941,171 B2 | 9/2005 | Mann et al. |
| 6,950,706 B2 | 9/2005 | Rodriguez et al. |
| 6,950,709 B2 | 9/2005 | Baudino |
| 6,981,314 B2 | 1/2006 | Black et al. |
| 6,985,088 B2 | 1/2006 | Goetz et al. |
| 6,993,384 B2 | 1/2006 | Bradley |
| 6,999,820 B2 | 2/2006 | Jordan |
| 7,009,313 B1 | 3/2006 | Parramon et al. |
| 7,010,356 B2 | 3/2006 | Jog et al. |
| 7,016,733 B2 | 3/2006 | Dublin et al. |
| 7,023,359 B2 | 4/2006 | Goetz et al. |
| 7,024,246 B2 | 4/2006 | Acosta et al. |
| 7,035,690 B2 | 4/2006 | Goetz |
| 7,039,470 B1 | 5/2006 | Wessman |
| 7,047,076 B1 | 5/2006 | Li et al. |
| 7,047,081 B2 | 5/2006 | Kuzma |
| 7,047,082 B1 | 5/2006 | Schrom et al. |
| 7,047,627 B2 | 5/2006 | Black et al. |
| 7,051,419 B2 | 5/2006 | Schrom et al. |
| 7,076,304 B2 | 7/2006 | Thompson |
| 7,099,718 B1 | 8/2006 | Thacker et al. |
| 7,107,102 B2 | 9/2006 | Daignault, Jr. et al. |
| 7,110,824 B2 | 9/2006 | Amundson et al. |
| 7,127,296 B2 | 10/2006 | Bradley |
| 7,127,297 B2 | 10/2006 | Law et al. |
| 7,127,298 B1 | 10/2006 | He et al. |
| 7,142,909 B2 | 11/2006 | Greenberg et al. |
| 7,146,223 B1 | 12/2006 | King |
| 7,155,278 B2 | 12/2006 | King et al. |
| 7,162,306 B2 | 1/2007 | Caby et al. |
| 7,174,215 B2 | 2/2007 | Bradley |
| 7,177,690 B2 | 2/2007 | Woods et al. |
| 7,177,691 B2 | 2/2007 | Meadows et al. |
| 7,177,702 B2 | 2/2007 | Wallace et al. |
| 7,181,286 B2 | 2/2007 | Sieracki et al. |
| 7,184,836 B1 | 2/2007 | Meadows et al. |
| 7,187,978 B2 | 3/2007 | Malek et al. |
| 7,206,642 B2 | 4/2007 | Pardo et al. |
| 7,211,103 B2 | 5/2007 | Greenberg et al. |
| 7,212,133 B2 | 5/2007 | Goetz et al. |
| 7,215,991 B2 | 5/2007 | Besson et al. |
| 7,225,032 B2 | 5/2007 | Schmeling et al. |
| 7,239,918 B2 | 7/2007 | Strother et al. |
| 7,239,920 B1 | 7/2007 | Thacker et al. |
| 7,248,929 B2 | 7/2007 | Meadows et al. |
| 7,254,443 B2 | 8/2007 | Jelen et al. |
| 7,254,445 B2 | 8/2007 | Law et al. |
| 7,254,446 B1 | 8/2007 | Erickson et al. |
| 7,263,406 B2 | 8/2007 | Toy et al. |
| 7,295,876 B1 | 11/2007 | Erickson |
| 7,295,878 B1 | 11/2007 | Meadows et al. |
| 7,310,873 B2 | 12/2007 | Pardo et al. |
| 7,317,948 B1 | 1/2008 | King et al. |
| 7,324,852 B2 | 1/2008 | Barolat et al. |
| 7,337,003 B2 | 2/2008 | Malinowski |
| 7,359,751 B1 | 4/2008 | Erickson et al. |
| 7,359,755 B2 | 4/2008 | Jones et al. |
| 7,363,079 B1 | 4/2008 | Thacker et al. |
| 7,369,897 B2 | 5/2008 | Boveja et al. |
| 7,376,466 B2 | 5/2008 | He et al. |
| 7,389,146 B2 | 6/2008 | Hanson et al. |
| 7,389,147 B2 | 6/2008 | Wahlstrand et al. |
| 7,428,438 B2 | 9/2008 | Parramon et al. |
| 7,437,193 B2 | 10/2008 | Parramon et al. |
| 7,437,197 B2 | 10/2008 | Harris et al. |
| 7,444,181 B2 | 10/2008 | Shi et al. |
| 7,444,184 B2 | 10/2008 | Boveja et al. |
| 7,463,927 B1 | 12/2008 | Chaouat |
| 7,471,986 B2 | 12/2008 | Hatlestad |
| 7,483,752 B2 | 1/2009 | Von Arx et al. |
| 7,489,966 B2 | 2/2009 | Leinders et al. |
| 7,496,404 B2 | 2/2009 | Meadows et al. |
| 7,499,755 B2 | 3/2009 | Cross, Jr. |
| 7,515,968 B2 | 4/2009 | Metzler et al. |
| 7,519,432 B2 | 4/2009 | Bolea et al. |
| 7,526,341 B2 | 4/2009 | Goetz et al. |
| 7,539,538 B2 | 5/2009 | Parramon et al. |
| 7,546,164 B2 | 6/2009 | King |
| 7,548,788 B2 | 6/2009 | Chinn et al. |
| 7,551,963 B2 | 6/2009 | Rusin et al. |
| 7,555,346 B1 | 6/2009 | Woods et al. |
| 7,571,001 B2 | 8/2009 | Thacker et al. |
| 7,580,753 B2 | 8/2009 | Kim et al. |
| 7,603,178 B2 | 10/2009 | North et al. |
| 7,603,179 B1 | 10/2009 | Grandhe |
| 7,613,518 B2 | 11/2009 | Qin et al. |
| 7,613,524 B2 | 11/2009 | Jordan |
| 7,617,006 B2 | 11/2009 | Metzler et al. |
| 7,630,749 B2 | 12/2009 | Squeri |
| 7,647,121 B2 | 1/2010 | Wahlstrand et al. |
| 7,650,192 B2 | 1/2010 | Wahlstrand |
| 7,657,319 B2 | 2/2010 | Goetz et al. |
| 7,658,196 B2 | 2/2010 | Ferreri et al. |
| 7,672,734 B2 | 3/2010 | Anderson et al. |
| 7,684,869 B2 | 3/2010 | Bradley et al. |
| 7,684,873 B2 | 3/2010 | Gerber |
| 7,697,995 B2 | 4/2010 | Cross, Jr. et al. |
| 7,706,888 B2 | 4/2010 | Jolly |
| 7,715,912 B2 | 5/2010 | Rezai et al. |
| 7,715,924 B2 | 5/2010 | Rezai et al. |
| 7,725,196 B2 | 5/2010 | Machado et al. |
| 7,729,781 B2 | 6/2010 | Swoyer et al. |
| 7,734,340 B2 | 6/2010 | De Ridder |
| 7,734,342 B2 | 6/2010 | Gielen et al. |
| 7,738,963 B2 | 6/2010 | Hickman et al. |
| 7,738,966 B2 | 6/2010 | Skubitz et al. |
| 7,742,810 B2 | 6/2010 | Moffitt et al. |
| 7,742,821 B1 | 6/2010 | Vamos et al. |
| 7,747,330 B2 | 6/2010 | Nolan et al. |
| 7,756,588 B2 | 7/2010 | Jog et al. |
| 7,761,167 B2 | 7/2010 | Bennett et al. |
| 7,761,170 B2 | 7/2010 | Kaplan et al. |
| 7,761,985 B2 | 7/2010 | Hegland et al. |
| 7,765,005 B2 | 7/2010 | Stevenson |
| 7,765,011 B2 | 7/2010 | Skubitz et al. |
| 7,769,462 B2 | 8/2010 | Meadows et al. |
| 7,787,960 B2 | 8/2010 | Lubenow et al. |
| 7,797,048 B2 | 9/2010 | Stevenson et al. |
| 7,797,054 B2 | 9/2010 | Skubitz et al. |
| 7,797,057 B2 | 9/2010 | Harris |
| 7,801,600 B1 | 9/2010 | Carbunaru et al. |
| 7,801,602 B2 | 9/2010 | McClure et al. |
| 7,801,615 B2 | 9/2010 | Meadows et al. |
| 7,801,621 B1 | 9/2010 | Thacker et al. |
| 7,803,021 B1 | 9/2010 | Brase |
| 7,805,189 B2 | 9/2010 | Stein et al. |
| 7,805,197 B2 | 9/2010 | Bradley |
| 7,813,796 B2 | 10/2010 | Greenberg et al. |
| 7,813,803 B2 | 10/2010 | Heruth et al. |
| 7,813,809 B2 | 10/2010 | Strother et al. |
| 7,818,068 B2 | 10/2010 | Meadows et al. |
| 7,831,306 B2 | 11/2010 | Finch et al. |
| 7,831,311 B2 | 11/2010 | Cross, Jr. et al. |
| 7,831,313 B2 | 11/2010 | Lauro |
| 7,835,795 B2 | 11/2010 | Alexander et al. |
| 7,844,343 B2 | 11/2010 | Wahlstrand et al. |
| 7,848,817 B2 | 12/2010 | Janzig et al. |
| 7,848,818 B2 | 12/2010 | Barolat et al. |
| 7,848,819 B2 | 12/2010 | Goetz et al. |
| 7,848,820 B2 | 12/2010 | Abrahamson |
| 7,853,330 B2 | 12/2010 | Bradley et al. |
| 7,856,277 B1 | 12/2010 | Thacker et al. |
| 7,860,568 B2 | 12/2010 | Deininger et al. |
| 7,860,570 B2 | 12/2010 | Whitehurst et al. |
| 7,872,884 B2 | 1/2011 | Parramon et al. |
| 7,881,796 B2 | 2/2011 | Scott et al. |
| 7,881,805 B2 | 2/2011 | Bradley et al. |
| 7,885,712 B2 | 2/2011 | Goetz et al. |
| 7,891,085 B1 | 2/2011 | Kuzma et al. |

(56) References Cited

U.S. PATENT DOCUMENTS

| | | |
|---|---|---|
| 7,899,542 B2 | 3/2011 | Cowan et al. |
| 7,904,148 B2 | 3/2011 | Greenberg et al. |
| 7,908,013 B2 | 3/2011 | Miesel et al. |
| 7,930,030 B2 | 4/2011 | Woods et al. |
| 7,930,037 B2 | 4/2011 | Heruth et al. |
| 7,930,039 B2 | 4/2011 | Olson |
| 7,933,656 B2 | 4/2011 | Sieracki et al. |
| 7,937,158 B2 | 5/2011 | Erickson et al. |
| 7,941,227 B2 | 5/2011 | Barker |
| 7,949,393 B2 | 5/2011 | Varrichio et al. |
| 7,957,797 B2 | 6/2011 | Bourget et al. |
| 7,957,809 B2 | 6/2011 | Bourget et al. |
| 7,957,814 B2 | 6/2011 | Goetz et al. |
| 7,970,003 B2 | 6/2011 | Holt |
| 7,974,703 B2 | 7/2011 | Goetz et al. |
| 7,974,705 B2 | 7/2011 | Zdeblick et al. |
| 7,979,126 B2 | 7/2011 | Payne et al. |
| 7,979,131 B2 | 7/2011 | Feler et al. |
| 7,979,133 B2 | 7/2011 | Feler et al. |
| 7,983,757 B2 | 7/2011 | Miyazawa et al. |
| 7,983,762 B2 | 7/2011 | Gliner et al. |
| 7,983,766 B1 | 7/2011 | Thacker et al. |
| 7,987,000 B2 | 7/2011 | Moffitt et al. |
| 7,991,482 B2 | 8/2011 | Bradley |
| 7,996,091 B2 | 8/2011 | Harris |
| 8,000,794 B2 | 8/2011 | Lozano |
| 8,000,800 B2 | 8/2011 | Takeda et al. |
| 8,005,547 B2 | 8/2011 | Forsberg et al. |
| RE42,682 E | 9/2011 | Barreras et al. |
| 8,019,427 B2 | 9/2011 | Moffitt |
| 8,019,438 B2 | 9/2011 | Johnson et al. |
| 8,019,439 B2 | 9/2011 | Kuzma et al. |
| 8,019,440 B2 | 9/2011 | Kokones et al. |
| 8,019,443 B2 | 9/2011 | Schleicher et al. |
| 8,032,224 B2 | 10/2011 | Miesel et al. |
| 8,036,737 B2 | 10/2011 | Goetz et al. |
| 8,036,747 B2 | 10/2011 | Thacker et al. |
| 8,036,754 B2 | 10/2011 | Lee et al. |
| 8,044,635 B2 | 10/2011 | Peterson |
| 8,046,073 B1 | 10/2011 | Pianca |
| 8,050,769 B2 | 11/2011 | Gharib et al. |
| 8,055,337 B2 | 11/2011 | Moffitt et al. |
| 8,065,013 B2 | 11/2011 | Bradley et al. |
| 8,073,542 B2 | 12/2011 | Doerr |
| 8,082,034 B2 | 12/2011 | Keacher |
| 8,082,039 B2 | 12/2011 | Kim et al. |
| 8,086,317 B2 | 12/2011 | Finch et al. |
| 8,086,318 B2 | 12/2011 | Strother et al. |
| 8,108,048 B2 | 1/2012 | Masoud |
| 8,108,049 B2 | 1/2012 | King |
| 8,108,051 B2 | 1/2012 | Cross, Jr. et al. |
| 8,108,052 B2 | 1/2012 | Boling |
| 8,112,159 B2 | 2/2012 | Harris et al. |
| 8,116,880 B2 | 2/2012 | Cross, Jr. |
| 8,121,697 B2 | 2/2012 | Greenberg et al. |
| 8,121,701 B2 | 2/2012 | Woods et al. |
| 8,121,702 B2 | 2/2012 | King |
| 8,126,567 B2 | 2/2012 | Gerber et al. |
| 8,131,358 B2 | 3/2012 | Moffitt et al. |
| 8,135,477 B2 | 3/2012 | Fattouh et al. |
| 8,140,168 B2 | 3/2012 | Olson et al. |
| 8,150,530 B2 | 4/2012 | Wesselink |
| 8,150,533 B2 | 4/2012 | Wessman |
| 8,155,750 B2 | 4/2012 | Jaax et al. |
| 8,155,752 B2 | 4/2012 | Aghassian et al. |
| 8,165,678 B2 | 4/2012 | Forsberg et al. |
| 8,170,674 B2 | 5/2012 | Pyles et al. |
| 8,170,675 B2 | 5/2012 | Alataris et al. |
| 8,175,719 B2 | 5/2012 | Shi et al. |
| 8,175,720 B2 | 5/2012 | Skelton et al. |
| 8,180,445 B1 | 5/2012 | Moffitt |
| 8,180,451 B2 | 5/2012 | Hickman et al. |
| 8,180,462 B2 | 5/2012 | Inman et al. |
| 8,185,207 B2 | 5/2012 | Molnar et al. |
| 8,185,212 B2 | 5/2012 | Carbunaru et al. |
| 8,195,297 B2 | 6/2012 | Penner |
| 8,195,304 B2 | 6/2012 | Strother et al. |
| 8,204,595 B2 | 6/2012 | Pianca et al. |
| 8,209,014 B2 | 6/2012 | Doerr |
| 8,209,021 B2 | 6/2012 | Alataris et al. |
| 8,214,051 B2 | 7/2012 | Sieracki et al. |
| 8,214,057 B2 | 7/2012 | Barolat |
| 8,224,453 B2 | 7/2012 | De Ridder |
| 8,285,388 B2 | 10/2012 | Wahlstrand |
| 8,340,779 B2 | 12/2012 | Harris et al. |
| 8,364,273 B2 | 1/2013 | DeRidder |
| 8,386,052 B2 | 2/2013 | Harris et al. |
| 8,401,655 B2 | 3/2013 | DeRidder |
| 8,412,349 B2 | 4/2013 | Barker |
| 8,467,883 B2 | 6/2013 | Chen et al. |
| 8,473,074 B2 | 6/2013 | North et al. |
| 8,494,640 B2 | 7/2013 | Peterson et al. |
| 8,515,555 B1 | 8/2013 | Jones |
| 8,554,337 B2 | 10/2013 | Barolat |
| 8,615,300 B2 | 12/2013 | Feler et al. |
| 8,634,893 B2 | 1/2014 | Skubitz et al. |
| 8,660,655 B2 | 2/2014 | Peterson et al. |
| 8,688,233 B2 | 4/2014 | Bradley et al. |
| 8,712,533 B2 | 4/2014 | Alataris et al. |
| 8,774,927 B2 | 7/2014 | DeRidder |
| 8,805,543 B2 | 8/2014 | Pianca et al. |
| 8,862,239 B2 | 10/2014 | Alataris et al. |
| 8,868,192 B2 | 10/2014 | Alataris et al. |
| 8,886,326 B2 | 11/2014 | Alataris et al. |
| 8,892,209 B2 | 11/2014 | Alataris et al. |
| 8,892,215 B2 | 11/2014 | Lipani |
| 8,903,508 B2 | 12/2014 | Feler |
| 8,934,981 B2 | 1/2015 | DeRidder |
| 8,942,821 B2 | 1/2015 | Barolat |
| 8,954,165 B2 | 2/2015 | Sharma et al. |
| 8,989,865 B2 | 3/2015 | Alataris et al. |
| 8,996,117 B2 | 3/2015 | Trier et al. |
| 9,005,503 B2 | 4/2015 | Govea |
| 9,026,228 B2 | 5/2015 | King |
| 9,044,610 B2 | 6/2015 | Rosenberg et al. |
| 9,067,056 B2 | 6/2015 | Sage |
| 9,079,018 B2 | 7/2015 | Olsen |
| 9,101,775 B2 | 8/2015 | Barker |
| 9,144,679 B2 | 9/2015 | Cullen et al. |
| 9,168,371 B2 | 10/2015 | Skubitz et al. |
| 9,186,510 B2 | 11/2015 | Gliner et al. |
| 9,199,074 B2 | 12/2015 | Pianca |
| 9,302,097 B2 | 4/2016 | Amrani |
| 9,302,113 B2 | 4/2016 | Ranu et al. |
| 9,327,127 B2 | 5/2016 | Alataris et al. |
| 9,327,128 B2 | 5/2016 | Ranu |
| 9,333,359 B2 | 5/2016 | Alataris et al. |
| 9,352,147 B2 | 5/2016 | Nguyen-Stella et al. |
| 9,399,132 B2 | 7/2016 | Parramon et al. |
| 9,409,019 B2 | 8/2016 | Walker et al. |
| 9,425,537 B2 | 8/2016 | Barker |
| 9,446,242 B2 | 9/2016 | Griffith |
| 9,462,398 B2 | 10/2016 | DeRidder |
| 10,016,602 B2 * | 7/2018 | Khalil ............... A61N 1/37241 |
| 2004/0102820 A1 | 5/2004 | Mouine et al. |
| 2004/0210245 A1 | 10/2004 | Erickson et al. |
| 2005/0033393 A1 | 2/2005 | Daglow |
| 2005/0143781 A1 | 6/2005 | Carbunaru et al. |
| 2005/0246004 A1 | 11/2005 | Cameron et al. |
| 2005/0288758 A1 | 12/2005 | Jones et al. |
| 2006/0127158 A1 | 6/2006 | Olson et al. |
| 2008/0294207 A1 | 11/2008 | Kast et al. |
| 2009/0099624 A1 | 4/2009 | Kokones et al. |
| 2009/0216306 A1 | 8/2009 | Barker |
| 2009/0270935 A1 | 10/2009 | Zhao et al. |
| 2010/0057177 A1 | 3/2010 | Moffitt et al. |
| 2010/0070010 A1 | 3/2010 | Simpson |
| 2010/0274336 A1 | 10/2010 | Nguyen-Stella et al. |
| 2011/0184486 A1 | 7/2011 | De Ridder |
| 2011/0208265 A1 | 8/2011 | Erickson et al. |
| 2011/0218549 A1 | 9/2011 | Barker |
| 2011/0270350 A1 | 11/2011 | Feler et al. |
| 2012/0209285 A1 | 8/2012 | Barker et al. |
| 2012/0232564 A1 | 9/2012 | Daglow |

(56) References Cited

U.S. PATENT DOCUMENTS

| | | |
|---|---|---|
| 2013/0204270 A1 | 8/2013 | Howard et al. |
| 2013/0204319 A1 | 8/2013 | Trier et al. |
| 2013/0261653 A1 | 10/2013 | Skubitz |
| 2013/0268041 A1 | 10/2013 | Schulte et al. |
| 2013/0274845 A1 | 10/2013 | Kokones et al. |
| 2014/0081351 A1 | 3/2014 | Feler et al. |
| 2014/0296936 A1 | 10/2014 | Alataris et al. |
| 2014/0343564 A1 | 11/2014 | Feler et al. |
| 2015/0005680 A1 | 1/2015 | Lipani |
| 2015/0005846 A1 | 1/2015 | Ranu et al. |
| 2015/0005860 A1 | 1/2015 | Howard et al. |
| 2015/0225609 A1 | 1/2015 | Govea |
| 2016/0001087 A1 | 1/2016 | Moffitt |
| 2016/0022994 A1 | 1/2016 | Moffitt et al. |
| 2016/0074663 A1 | 3/2016 | DeRidder |
| 2016/0166835 A1 | 6/2016 | DeRidder |
| 2016/0166836 A1 | 6/2016 | Shanahan et al. |
| 2016/0206873 A1 | 7/2016 | Hou et al. |
| 2016/0206883 A1 | 7/2016 | Bornzin et al. |
| 2016/0206891 A1 | 7/2016 | Howard et al. |
| 2016/0213314 A1 | 7/2016 | Zuckerman-Stark et al. |
| 2016/0213915 A1 | 7/2016 | Amrani |
| 2016/0250461 A1 | 9/2016 | Dubuclet |
| 2016/0256679 A1 | 9/2016 | Nguyen-Stella et al. |
| 2016/0279418 A1 | 9/2016 | Courtine et al. |
| 2016/0287864 A1 | 10/2016 | North et al. |
| 2016/0303374 A1 | 10/2016 | Alataris et al. |

\* cited by examiner

SPINAL CORD STIMULATOR SYSTEM

CROSS REFERENCE TO RELATED APPLICATIONS

This application is a continuation of U.S. patent application Ser. No. 14/213,266, filed on Mar. 14, 2014 (published as U.S. Patent Publication No. 2014-0277264), which is a non-provisional application that claims priority to provisional application No. 61/792,654 filed on Mar. 15, 2013, all of which are incorporated in their entirety herein.

TECHNICAL FIELD

This disclosure relates to stimulators using electrical pulses in a medical context, and more particularly, applying electrical pulse stimulators to the spinal cord to control pain.

BACKGROUND

A Spinal Cord Stimulator (SCS) is used to exert pulsed electrical signals to the spinal cord to control chronic pain. Spinal cord stimulation, in the simplest form, consists of stimulating electrodes, implanted in the epidural space, an electrical pulse generator, implanted in the lower abdominal area or gluteal region, conducting wires connecting the electrodes to the generator, the generator remote control, and the generator charger. Spinal cord stimulation has notable analgesic properties and, at the present, is used mostly in the treatment of failed back surgery syndrome, complex regional pain syndrome and refractory pain due to ischemia.

Electrotherapy of pain by neurostimulation began shortly after Melzack and Wall proposed the gate control theory in 1965. This theory proposed that nerves carrying painful peripheral stimuli and nerves carrying touch and vibratory sensation both terminate in the dorsal horn (the gate) of spinal cord. It was hypothesized that input to the latter could be manipulated to "close the gate" to the former. As an application of the gate control theory, Shealy et al. implanted the first spinal cord stimulator device directly on the dorsal column for the treatment of chronic pain in 1971.

Spinal cord stimulation does not eliminate pain. The electrical impulses from the stimulator override the pain messages so that the patient does not feel the pain intensely. In essence, the stimulator masks the pain. The stimulation must be done on a trial basis first before the stimulator is permanently implanted. Implanting the stimulator is typically done using a local anesthetic and a sedative. The physician will first insert a trial stimulator through the skin (percutaneously) to give the treatment a trial run. (A percutaneous stimulator tends to move from its original location, so it is considered temporary.) If the trial is successful, the physician can then implant a more permanent stimulator. The stimulator itself is implanted under the skin of the abdomen, and the leads are inserted under the skin to the point where they are inserted into the spinal canal. This placement in the abdomen is a more stable, effective location. The leads, which consist of an array of electrodes, could be percutaneous type or paddle type. Percutaneous electrodes are easier to insert in comparison with paddle type, which are inserted via incision over spinal cord and laminectomy.

There are a number of problems that exist in currently available SCS systems that limit the full benefits of dorsal column stimulation from an effectiveness and patient user friendly perspective. For example, SCS systems are limited at the moment to only 16 electrodes with a maximum of 16 independent current sources. In addition, current SCS systems have complicated trialing methods that involve multiple gadgets and hardware even in current wireless SCS systems. Patients at the moment must carry an independent remote control in order to control the IPG in their daily lives.

SUMMARY

The present invention emphasizes the following specific features included within a spinal cord stimulation system: (1) a recharging system with self alignment, (2) a system for mapping current fields using a completely wireless system, (3) multiple independent electrode stimulation outsource, and (4) IPG control through a software on generic Smartphone/mobile device and tablet hardware during trial and permanent implants. Current SCS systems include multiple electrodes, multiple, independently programmable, stimulation channels within an implantable pulse generator (IPG) which channels can provide concurrent, but unique stimulation fields, permitting virtual electrodes to be realized. Current SCS systems include a replenishable power source (e.g., rechargeable battery), that may be recharged using transcutaneous power transmissions between antenna coil pairs. An external charger unit, having its own rechargeable battery can be used to charge the IPG replenishable power source. A real-time dock can provide an auto-run schedule for daily stimulation. An included bi-directional telemetry link in the system informs the patient or clinician the status of the system, including the state of charge of the IPG battery. Other processing circuitry in current IPG allows electrode impedance measurements to be made. Further circuitry in the external battery charger can provide alignment detection for the coil pairs. FIG. 1 depicts a SCS system, as described herein, for use during the trial in the operating room and the permanent implantation.

The newly invented SCS system is superior to existing systems. More particularly, the SCS system of the present invention provides a stimulus to a selected pair or group of a multiplicity of electrodes, e.g., 32 electrodes, grouped into multiple channels, e.g., 6 channels. Advantageously, each electrode is able to produce a programmable constant output current of at least 12 mA over a range of output voltages that may go as high as 16 volts. Further, in a preferred embodiment, the implant portion of the SCS system includes a rechargeable power source, e.g., one or more rechargeable batteries. The SCS system herein described requires only an occasional recharge; the implanted portion is smaller than existing implant systems and also has a self aligning feature to guide the patient while placing the charger over the implanted IPG for the most efficient power recharge; the SCS system has a life of at least 10 years at typical settings; the SCS system offers a simple connection scheme for detachably connecting a lead system thereto; and the SCS system is extremely reliable.

As a feature of the invention, each of the electrodes included within the stimulus channels may not only deliver up to 12.7 mA of current over the entire range of output voltages, but also may be combined with other electrodes to deliver even more current up to a maximum of 20 mA. Additionally, the SCS system provides the ability to stimulate simultaneously on all available electrodes in the SCS system. That is, in operation, each electrode is grouped with at least one additional electrode form one channel. The system allows the activation of electrodes to at least 10 channels. In one embodiment, such grouping is achieved by a low impedance switching matrix that allows any electrode contact or the system case (which may be used as a common, or indifferent, electrode) to be connected to any other electrode. In another embodiment, programmable output current DAC's (digital-to-analog converters) are connected to each electrode node, so that, when enabled, any electrode node can be grouped with any other electrode node that is enabled at the same time, thereby eliminating the need for the low impedance switching matrix. This advantageous feature thus allows the clinician to provide unique electrical stimulation fields for each current channel, heretofore unavailable with other "multichannel" stimulation systems (which "multi-channel" stimulation systems are really multiplexed single channel stimulation systems). Moreover, this feature, combined with multicontact electrodes arranged in two or three dimensional arrays, allows "virtual electrodes" to be realized, where a "virtual" electrode comprises an electrode that appears to be at a certain physical location, but really is not physically located at the apparent location. Rather, the virtual electrode results from the vector combination of electrical fields from two or more electrodes that are activated simultaneously.

As an additional feature of the invention, the SCS system includes an implantable pulse generator (IPG) that is powered by a rechargeable internal battery, e.g., a rechargeable Lithium Ion battery providing an output voltage that varies from about 4.1 volts, when fully charged, to about 3.5 volts.

A number of different new invented components are part of the newly invented SCS system herein. There are a number of different sub-components for each newly invented component that are part of the newly invented SCS system. Starting from a top hierarchal level, the newly invented SCS system is composed of an IPG, Trial generator, Wireless Dongle, IPG Charger, Clinical Programmer Software, Patient Programmer Software, Leads (percutaneous and paddle), Lead anchors, Lead Splitters, Lead Extensions, and Accessories. FIG. 1 depicts the components during trial and permanent implantation.

DETAILED DESCRIPTION

Implantable Pulse Generator (IPG)

Figure 1:
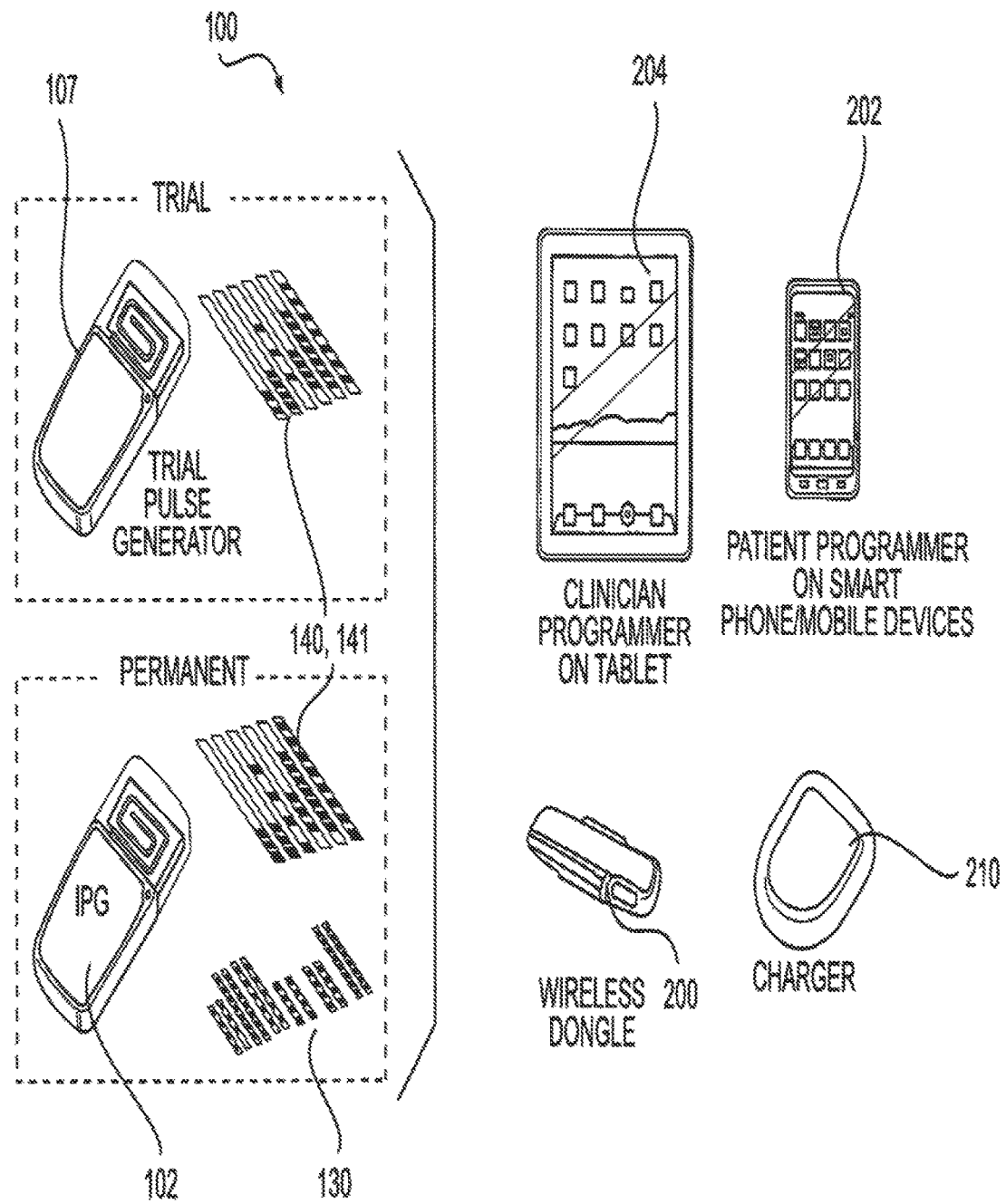
FIG. 1 depicts various components that can be included in a spinal cord stimulation system, according to an embodiment.

The spinal cord stimulator (SCS) is an implantable device used to deliver electrical pulse therapy to the spinal cord in order to treat chronic pain. The implantable components of the system consist of an Implantable Pulse Generator (IPG) and a multitude of stimulation electrodes. The IPG is implanted subcutaneously, no more than 30 mm deep in an area that is comfortable for the patient while the stimulation electrodes are implanted directly in the epidural space. The electrodes are wired to the IPG via leads which keep the stimulation pulses isolated from each other in order to deliver the correct therapy to each individual electrode.

The therapy delivered consists of electrical pulses with controlled current amplitude ranging from +12.7 to −12.7 mA (current range 0-25.4 mA). These pulses can be programmed in both length and frequency from 100 to 20000 and 0.5 Hz to 1200 Hz. At any given moment, the sum of the currents sourced from the anodic electrodes must equal the sum of the currents sunk by the cathodic electrodes. In addition, each individual pulse is bi-phasic, meaning that once the initial pulse finishes another pulse of opposite amplitude is generated after a set holdoff period. The electrodes may be grouped into stimulation sets in order to deliver the pulses over a wider area or to target specific areas, but the sum of the currents being sourced at any one given time may not exceed 20 mA. A user can also program different stim sets (up to eight) with different parameters in order to target different areas with different therapies.

The IPG consists of two major active components, a battery, antenna, some support circuitry, and a multitude of output capacitors. The first of the major active components is the microcontroller transceiver. It is responsible for receiving, decoding, and execution both commands and requests from the external remote. If necessary it passes these commands or requests onto the second major component, the ASIC. The ASIC receives the digital data from the microcontroller and performs the entire signal processing to generate the signals necessary for stimulation. These signals are then passed onto the stimulation electrodes in the epidural space.

The ASIC itself is by far the most complex piece of the design. It is made up of a digital section and an analog section. The digital section if further divided into multiple sections including; Timing Generators, Arbitration Control, Pulse Burst Conditioner, and Electrode Logic. The analog section has the simple job of taking the incoming pulses from the digital section and simply amplifying them in order to deliver the correct therapy. There are also a multitude of digital register memory elements that each section utilizes, both digital and analog.

The digital elements in the ASIC are all made up of standard subsets of digital logic including logic gates, timers, counters, registers, comparators, flip-flips, and decoders. These elements are ideal for processing the stimulation pulses as all of them can function extremely fast—orders of magnitudes faster than the required pulse width. The one drawback is that they must all function at one single voltage, usually 5.0, 3.3, 2.5, or 1.8 volts. Therefore they are not suitable for the final stage in which the pulses are amplified in order to deliver the constant current pulses.

The timing generators are the base of each of the stimulation sets. It generates the actual rising and falling edge triggers for each phase of the bi-phasic pulse. It accomplishes this by taking the incoming clock that is fed from the microcontroller and feeding it into a counter. For the purpose of this discussion, assume the counter simply counts these rising clock edges infinitely. The output of the counter is fed into six different comparators. The comparators other input is connected to specific registers that are programmed by the microcontroller. When the count equals the value stored in the register, the comparator asserts a positive signal.

The first comparator is connected to the SET signal of a SR flip flop. The SR flip flop stays positive until the RESET signal is asserted, which the second comparator is connected to. The output of the SR flip flop is the first phase of the bi-phasic pulse. Its rising & falling edges are values stored in the registers and programmed by the microcontroller. The third and fourth comparators & registers work in exactly the same way to produce the second phase of the bi-phasic pulse using the second SR flip flop.

The fifth comparator is connected the RESET of the final SR-Flip flop in the timing generator. This flip flop is SET by the first comparator, which is the rising edge of the first pulse. The RESET is then triggered by the value the microprocessor programmed into the register connected to the comparator. This allows for a 'holdoff' period after the falling edge of the second pulse. The output of this third SR flip flop can be thought of as an envelope of the biphasic pulses indicating when this particular timing generator is active.

The final comparator of the system is once again connected to a register that stores the frequency values from the microprocessor. Essentially when the count reaches this value it triggers the comparator which is fed back to the counter to reset it to zero and beginning the entire pulse generation cycle again. The ASIC may contain many of these timing generators as each can control anywhere from two to all of the electrodes connected to the IPG at a time. However, when there is more than one timing generator and multiple channels have been actively programmed then there needs to be a mechanism for suppressing a second channel from turning on when another is already active.

This brings us to the next circuit block contained in the IPG, the arbitrator. The arbitrator functions by looking at each of the timing generators' envelope signals and makes sure only one can be active at a time. If a second tries to activate then the arbitrator suppresses that signal.

It accomplishes this by bringing each of the channel envelope signals into a rising edge detection circuit. Once one is triggered it is fed into the SET pin of an SR flip flop. The output of this SR-flip flop is fed into all of the other rising edge detectors in order to suppress them from triggering. The channel envelope signal is also fed into a falling-edge detector which is then fed into the RESET of the same SR flip flop. The output of the SR flip flops are then connected to switches whose outputs are all tied together that turn on/off that channels particular biphasic pulse train. Therefore the output of this circuit element is a single bi-phasic pulse train and a signal designating which timing generator that particular pulse train is sourced from. Essentially, the circuit looks for a channel to go active. Once it finds one it suppresses all others until that channel becomes inactive.

The next section of the circuit works very similarly to the timing generators to create a high speed burst pulse train that is then combined with the stimulation pulse train to create a bursted bi-phasic pulse train if desired.

It accomplishes this by taking the incoming clock that is fed from the microcontroller and feeding it into a counter. For the purpose of this discussion, assume the counter simply counts these rising clock edges infinitely. The counter is only active when during a single phase of the bi-phasic signal and begins counting as soon as the rising edge is detected. The output of the counter is fed into a comparator, along with a microcontroller-programmed register, whose output is connected to the reset pin on the counter. Therefore this counter will simply count to a programmed value & reset. This programmed value is the burst frequency.

The output of the comparator is then fed into an edge detection circuit and then a flip flop that combines it with the actual stimulation pulse train to create a single phase bursted stimulation pulse. The entire circuit is duplicated for the second phase of the signal resulting in the desired bursted bi-phasic pulse train. The stimulation signal is now ready to be handed over to the electrode logic stage.

The electrode logic conditions and directs the bi-phasic signals to the analog section of the ASIC. At this point, the bi-phasic signals contain all of the pertinent timing information, but none of the required amplitude information. The incoming signals include the bi-phasic pulse train and another signal designating which timing generator the current active train came from. Each electrode logic cell has a register for each timing generator that stores this particular electrode's amplitude values for that timing generator. The electrode logic cell uses the designation signal to determine which register to pull the amplitude values from, e.g. if the third timing generator is passed through the arbitration circuit then the electrode logic would read the value from the third register.

Once the value is pulled from the register, it goes through a series of logic gates. The gates first determine that the electrode should be active. If not, they proceed no further and do not activate the analog section of the electrode output, thereby saving precious battery power. Next they determine if this particular electrode is an anode or cathode. If it is deemed to be an anode, the electrode logic passes the amplitude information and the biphasic signal to the positive current (digital to analog converter) DAC in the analog section of the ASIC. If it is deemed to be a cathode, the electrode logic passes the amplitude information and the biphasic signal to the negative current DAC in the analog section of the ASIC. The electrode logic circuit must make these decisions for each phase of the bi-phasic signal as every electrode will switch between being an anode and a cathode.

The analog elements in the ASIC are uniquely designed in order to produce the desired signals. The basis of analog IC design is the field effect transistor (FET) and the type of high current multiple output design required in SCS means that the bulk of the silicon in the ASIC will be dedicated to the analog section.

The signals from the electrode output are fed into each current DAC when that specific electrode should be activated. Each electrode has a positive and a negative current DAC, triggered by the electrode logic and both are never active at the same time. The job of each current DAC is, when activated, to take the digital value representing a stimulation current amplitude and produce an analog representation of this value to be fed into the output stage. This circuit forms half of the barrier between the digital and analog sections of the ASIC.

The digital section of the ASIC is built upon a technology that only allows small voltages to exist. In moving to the analog section, the output of the current DAC (which is a low level analog signal) must be amplified to a higher voltage for use in the analog section. The circuit that performs this task is called a power level shifter. Because this circuit is built upon two different manufacturing technologies and requires high precision analog circuits built upon a digital base, it is extremely difficult to implement.

Once the voltages have been converted for usage in the analog portion of the ASIC they are passed on to the output current stages. There are two current sources per electrode output. One will source a positive current and one will sink a negative current, but they will never both be active simultaneously. The current sources themselves are made up of analog elements similar to a Howland current source. There is an input stage, and amplification stage with feedback through a sensing component to maintain the constant current. The input stage takes the analog voltage values from the power level shifter and produces an output pulse designated for the amplifier. The amplifier then creates the pulses of varying voltages but constant current flow. The sources are capable of sourcing or sinking up to 12.7 mA at 0.1 mA resolution into a load of up to 1.2 k Ohms. This translates into range of 15 volts, which will vary depending on the load in order to keep the current constant.

The microcontroller to ASIC interface is designed to be as simple as possible with minimal bus 'chatter' in order to save battery life. The ASIC will essentially be a collection of registers programmed via a standard I²C or SPI bus. Since the ASIC is handling all the power management, there will also be a power good (PG) line between the two chips in order to let the microcontroller know when it is safe to power up. The ASIC will also need to use a pin on the microcontroller in order to generate a hardware interrupt in case anything goes awry in the ASIC. The final connection is the time base for all of the stimulation circuitry. The ASIC will require two clocks, one for its internal digital circuitry which will be fed directly from the microcontroller clock output, and one to base all stimulation off of which will need to be synthesized by the microcontroller and fed to the ASIC. All commands and requests to the ASIC will be made over the I²C or SPI bus and will involve simply reading a register address or writing to a register. Even when the ASIC generates a hardware interrupt, it will be the responsibility of the microcontroller to poll the ASIC and determine the cause of the interrupt.

The wireless interface is based upon the FCCs MedRadio standard operating in the 402-405 Mhz range utilizing up to 10 channels for telemetry. The protocol is envisioned to be very simple once again in order to minimize transmission and maximize battery life. All processing will take place on the user remote/programmer and the only data transmitted is exactly what will be used in the microcontroller to ASIC bus. That is, all of the wireless packets will contain necessary overhead information along with only a register address, data to store in the register, and a command byte instructing the microcontroller what to do with the data. The overhead section of the wireless protocol will contain synchronization bits, start bytes, an address which is synchronized with the IPG's serial number, and a CRC byte to assure proper transmission. It is essential to keep the packet length as small as possible in order to maintain battery life. Since the IPG cannot listen for packets all the time due to battery life, it cycles on for a duty cycle of less than 0.05% of the time. This time value can be kept small as long as the data packets are also small. The user commands needed to run the system are executed by the entire system using flows.

The IPG uses an implantable grade Li ion battery with 215 mAHr with zero volt technology. The voltage of the battery at full capacity is 4.1 V and it supplies current only until it is drained up to 3.3 V which is considered as 100% discharged. The remaining capacity of the battery can be estimated at any time by measuring the voltage across the terminals. The maximum charge rate is 107.5 mA. A Constant Current, Constant Voltage (CCCV) type of regulation can be applied for faster charging of the battery.

The internal secondary coil L2 is made up of 30 turns of 30 AWG copper magnet wires. The ID, OD, and the thickness of the coil are 30, 32, and 2 mm, respectively. Inductance L2 is measured to be 58 uH, a 80 nF capacitor is connected to it to make a series resonance tank at 74 kHz frequency. Two types of rectifiers are considered to convert the induced AC into usable DC-a bridge full wave rectifier and a voltage doubler kind of full wave rectifier. To get higher voltage, later type of rectifier is used in this design. The rectifier is built with high speed Schottky diodes to improve its function at high frequencies of the order 100 kH. A Zener diode and also a 5V voltage regulator are used for regulation. This circuit will be able to induce AC voltage, rectify to DC, regulate to 5V and supply 100 mA current to power management IC that charges the internal battery by CCCV regulation.

The regulated 5V 100 mA output from the resonance tank is fed to, for example, a Power Management Integrated Circuit (PMIC) MCP73843. This particular chip was specially designed by Microchip to charge a Li ion battery to 4.1 V by CCCV regulation. The fast charge current can be regulated by changing a resistor; it is set to threshold current of 96 mA in this circuit. The chip charges the battery to 4.1V as long as it receives current more than 96 mA. However, if the supply current drops below 96 mA, it stops to charge the battery until the supply is higher than 96 again. For various practical reasons, if the distance between the coils increases, the internal secondary coil receives lesser current than the regulated value, and instead of charging the battery slowly, it pauses the charging completely until it receives more than 96 mA.

All the functions of the IPG are controlled from outside using a hand held remote controller specially designed for this device. Along with the remote control, an additional control is desirable to operate the IPG if the remote control was lost or damaged. For this purpose a Hall effect based magnet switch was incorporated to either turn ON or turn OFF the IPG using an external piece of magnet. Magnet switch acts as a master control for the IPG to turn on or off. A south pole of sufficient strength turns the output on and a north pole of sufficient strength is necessary to turn the output off. The output is latched so that the switch continues to hold the state even after the magnet is removed from its vicinity.

Figure 2:
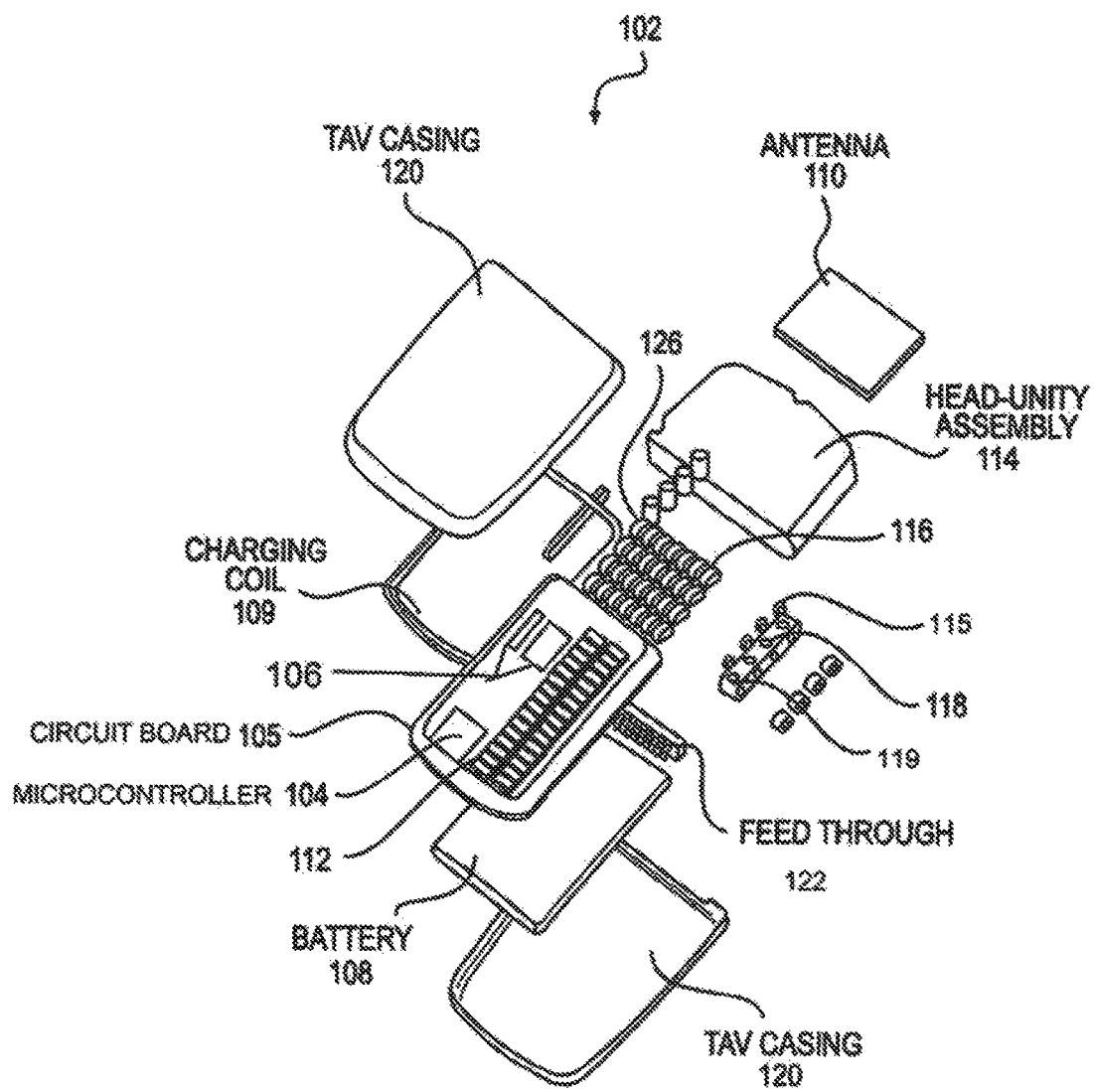
FIG. 2 depicts an exploded view of an implantable pulse generator (IPG) assembly, according to an embodiment.

The IPG is an active medical implant that generates an electrical signal that stimulates the spinal cord. The signal is carried through a stimulation lead that plugs directly into the IPG. The IPG recharges wirelessly through an induction coil, and communicates via RF radio antenna to change stimulation parameters. The IPG is implanted up to 3 cm below the surface of the skin and is fixed to the fascia by passing two sutures through holes in the epoxy header. The leads are electrically connected to the IPG through a lead contact system, a cylindrical spring-based contact system with inter-contact silicone seals. The leads are secured to the IPG with a set screw that actuates within locking housing. Set screw compression on the lead's fixation contact is governed by a disposable torque wrench. The wireless recharging is achieved by aligning the exterior induction coil on the charger with the internal induction coil within the IPG. The RF antenna within the remote's dongle communicates with the RF antenna in the IPG's epoxy header. FIG. 2 illustrates an exploded view of the IPG assembly.

Figure 3:
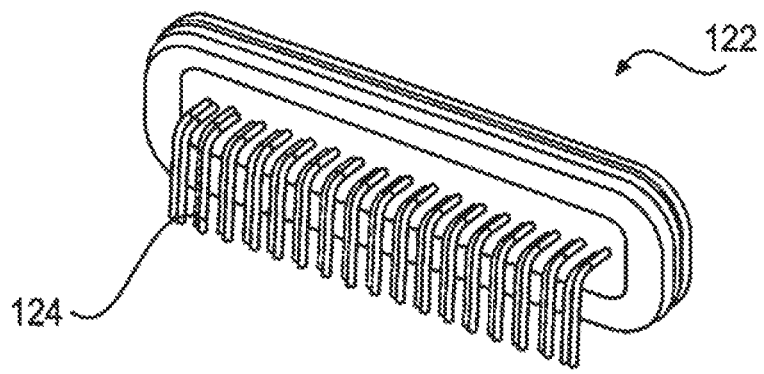
FIG. 3 depicts a feedthrough assembly of an implantable pulse generator (IPG) assembly, according to an embodiment.

The IPG is an assembly of a hermetic titanium (6Al-4V) casing which houses the battery, circuitry, and charging coil, with an epoxy header, which houses the lead contact assembly, locking housing, and RF antenna. The internal electronics are connected to the components within the epoxy head through a hermetic feedthrough, as shown in FIG. 3. The feedthrough is a titanium (6Al-4V) flange with an alumina window and gold trimming. Within the alumina window are thirty-four platinum-iridium (90-10) pins that interface internally with a direct solder to the circuit board, and externally with a series of platinum iridium wires laser-welded to the antenna and lead contacts. The IPG has the ability to interface with 32 electrical contacts, which are arranged in four rows of eight contacts. Thirty two of the feedthrough's pins will interface with the contacts, while two will interface with the antenna, one to the ground plane and one to the antenna feed.

Figure 4:
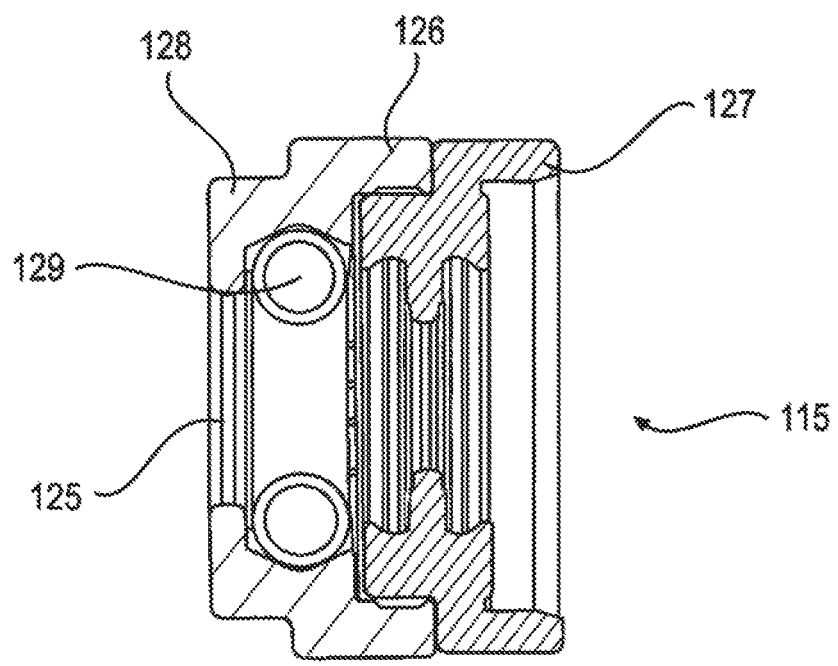
FIG. 4 depicts a lead contact system of an implantable pulse generator (IPG) assembly, according to an embodiment.
Figure 5:
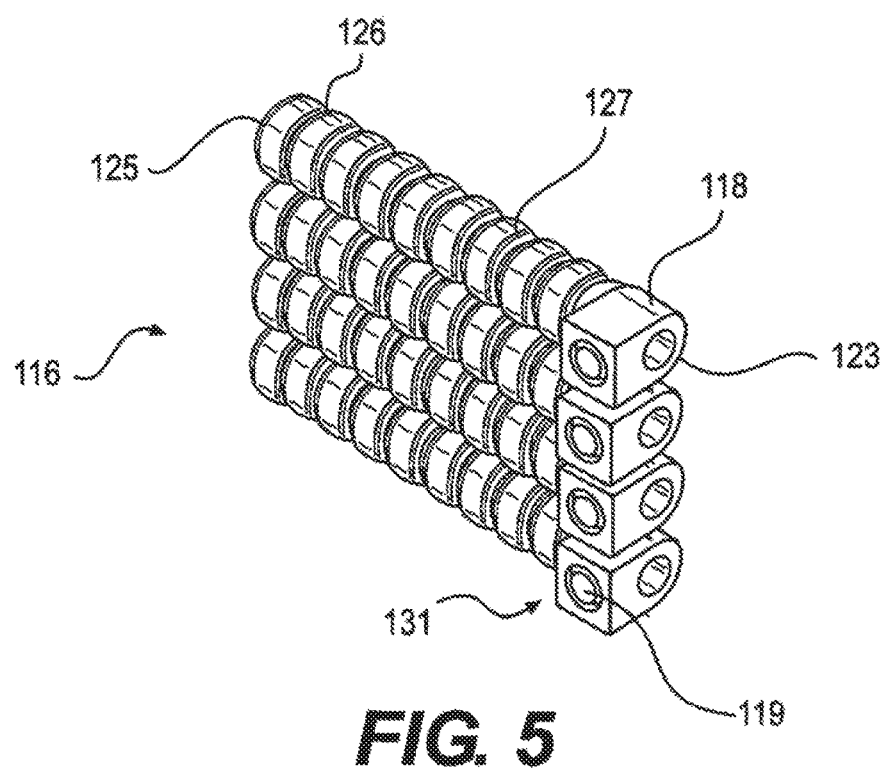
FIG. 5 depicts a lead contact assembly of an implantable pulse generator (IPG) assembly, according to an embodiment.
Figure 6:
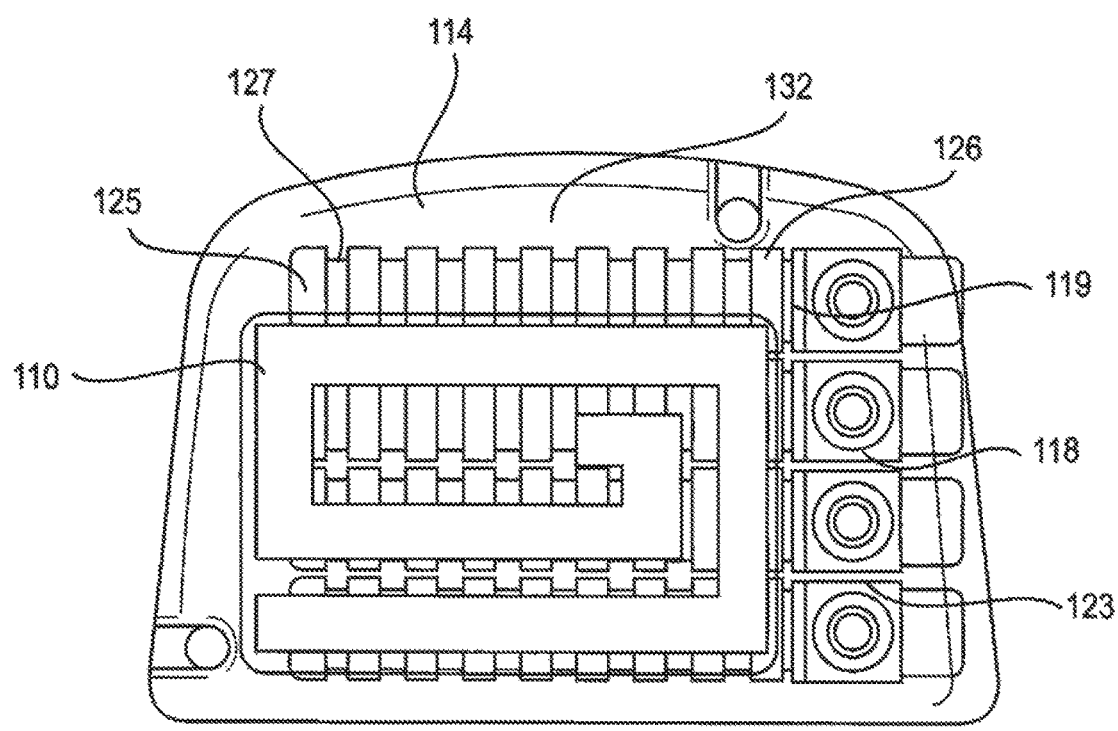
FIG. 6 depicts a head unit assembly of an implantable pulse generator (IPG) assembly, according to an embodiment.
Figure 7:
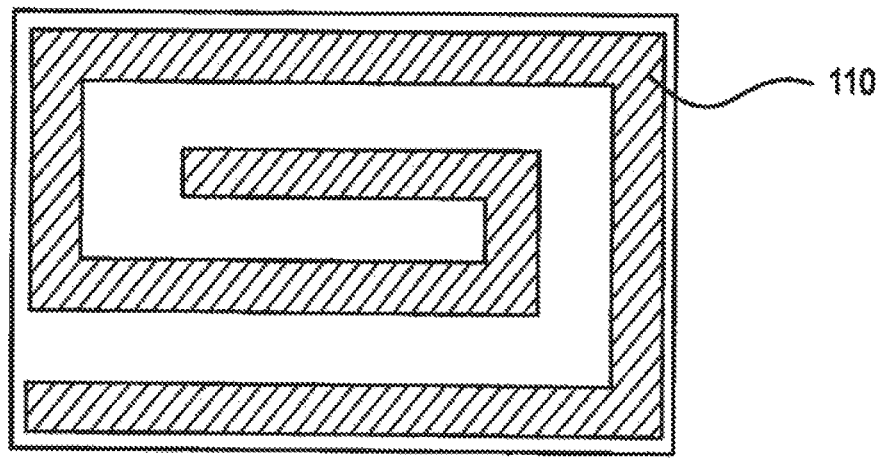
FIG. 7 depicts an RF antenna of an implantable pulse generator (IPG) assembly, according to an embodiment.

FIGS. 4 and 5 depict a lead contact system and assembly, respectively. The lead contacts consist of an MP35N housing with a platinum-iridium 90-10 spring. Each contact is separated by a silicone seal. At the proximal end of each stack of 8 contacts is a titanium (6Al-4V) cap which acts as a stop for the lead. At the distal end is a titanium (6Al-4V) set screw and block for lead fixation. At the lead entrance point there is a silicone tube which provides strain relief as the lead exits the head unit, and above the set screw is another silicone tube with a small internal canal which allows the torque wrench to enter but does not allow the set screw to back out. In addition to the contacts and antenna, the header also contains a radiopaque titanium (6Al-4V) tag which allows for identification of the device under fluoroscopy. The overmold of the header is Epotek 301, a two-part, biocompatible epoxy. FIGS. 4, 5, 6, and 7 depict illustrations of lead contact system, lead contact assembly, head unit assembly, and RF antenna, respectively.

Internal to the titanium (6Al-4V) case are the circuit board, battery, charging coil, and internal plastic support frame. The circuit board will be a multi-layered FR-4 board with copper traces and solder mask coating. Non-solder masked areas of the board will be electroless nickel immersion gold. The implantable battery, all surface mount components, ASIC, microcontroller, charging coil, and feedthrough will be soldered to the circuit board. The plastic frame, made of either polycarbonate or ABS, will maintain the battery's position and provide a snug fit between the circuitry and case to prevent movement. The charging coil is a wound coated copper.

Leads

Figure 8:
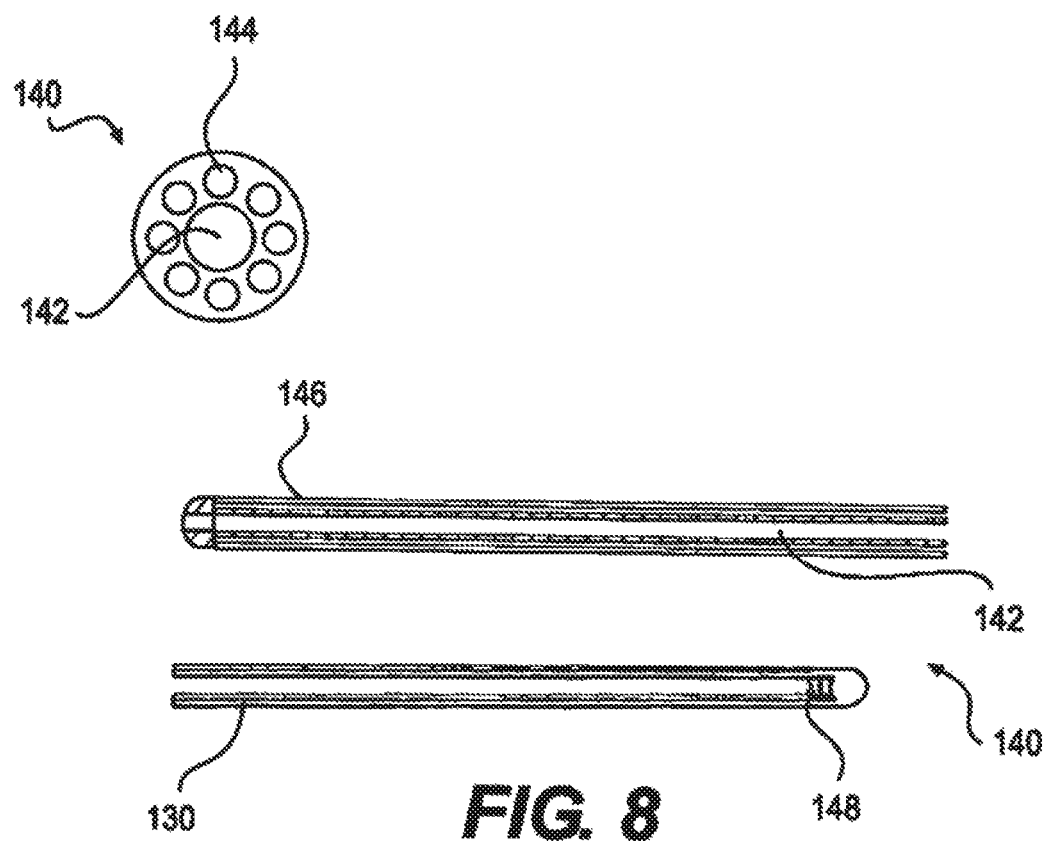
FIG. 8 depicts a percutaneous lead, according to an embodiment.

The percutaneous stimulation leads, as depicted in FIG. 8, are a fully implantable electrical medical accessory to be used in conjunction with the implantable SCS. The primary function of the lead is to carry electrical signals from the IPG to the target stimulation area on the spinal cord. Percutaneous stimulation leads provide circumferential stimulation. The percutaneous stimulation leads must provide a robust, flexible, and bio-compatible electric connection between the IPG and stimulation area. The leads are surgically implanted through a spinal needle, or epidural needle, and are driven through the spinal canal using a steering stylet that passes through the center of the lead. The leads are secured mechanically to the patient using either an anchor or a suture passed through tissue and tied around the body of the lead. The leads are secured at the proximal end with a set-screw on the IPG which applies radial pressure to a blank contact on the distal end of the proximal contacts.

The percutaneous stimulation leads consist of a combination of implantable materials. Stimulation electrodes at the distal end and electrical contacts at the proximal end are made of a 90-10 platinum-iridium alloy. This alloy is utilized for its bio-compatibility and electrical conductivity. The electrodes are geometrically cylindrical. The polymeric body of the lead is polyurethane, which is chosen for its bio-compatibility, flexibility, and high lubricity to decrease friction while being passed through tissue. The polyurethane tubing has a multi-lumen cross section, with one center lumen and eight outer lumens. The center lumen acts as a canal to contain the steering stylet during implantation, while the outer lumens provide electrical and mechanical separation between the wires that carry stimulation from the proximal contacts to distal electrodes. These wires are a bundle of MP35N strands with a 28% silver core. The wires are individually coated with ethylene tetrafluoroethylene (ETFE), to provide an additional non-conductive barrier. The wires are laser welded to the contacts and electrodes, creating an electrical connection between respective contacts on the proximal and distal ends. The leads employ a platinum-iridium plug, molded into the distal tip of the center lumen to prevent the tip of the steering stylet from puncturing the distal tip of the lead. Leads are available in a variety of 4 and 8 electrode configurations. These leads have 4 and 8 proximal contacts (+1 fixation contact), respectively. Configurations vary by electrode number, electrode spacing, electrode length, and overall lead length.

Figure 9:
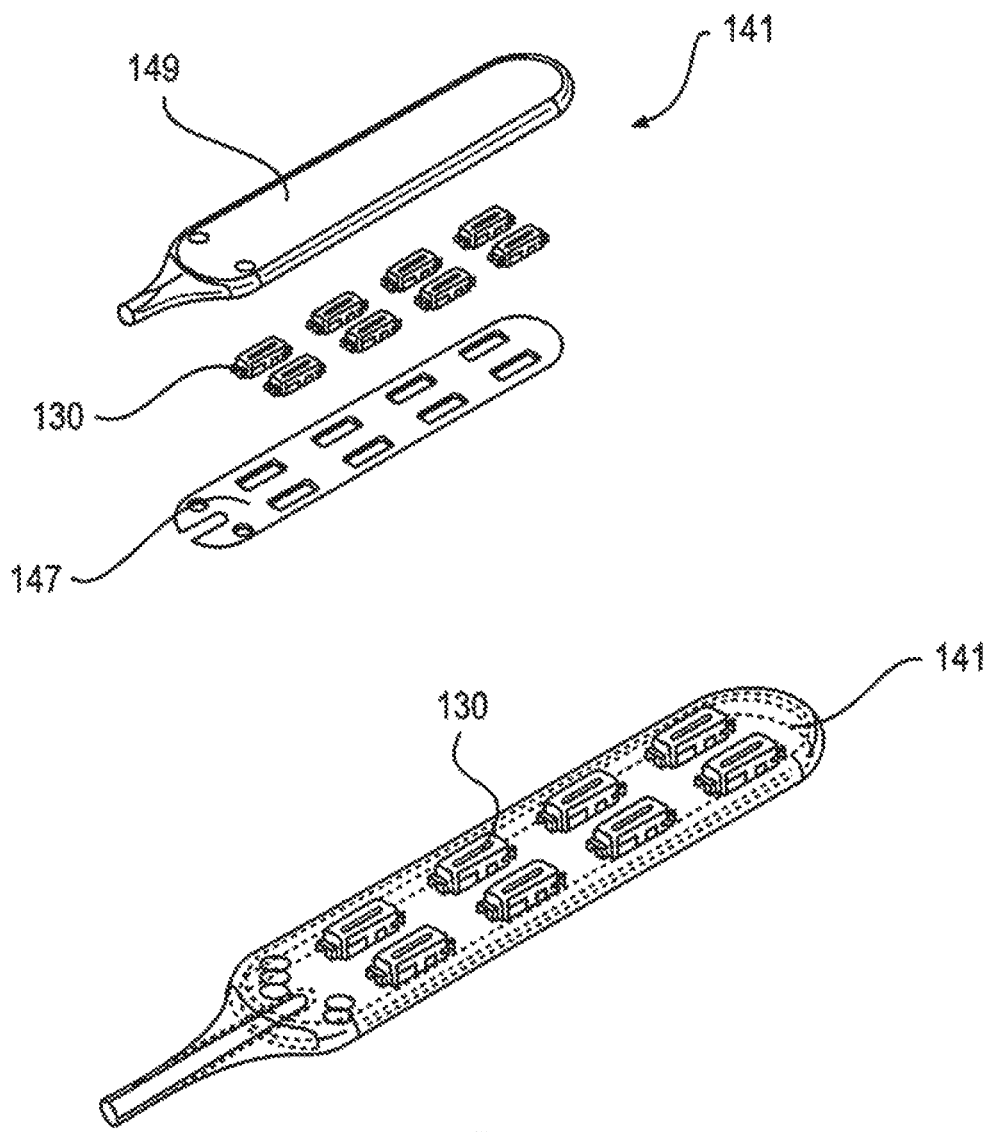
FIG. 9 depicts a paddle lead, according to an embodiment.

The paddle stimulation leads, as depicted in FIG. 9, are a fully implantable electrical medical accessory to be used in conjunction with the implantable SCS. The primary function of the paddle lead is to carry electrical signals from the IPG to the target stimulation area on the spinal cord. The paddle leads provide uni-direction stimulation across a 2-dimensional array of electrodes, allowing for greater precision in targeting stimulation zones. The paddle stimulation leads must provide a robust, flexible, and bio-compatible electric connection between the IPG and stimulation area. The leads are surgically implanted through a small incision, usually in conjunction with a laminotomy or laminectomy, and are positioned using forceps or a similar surgical tool. The leads are secured mechanically to the patient using either an anchor or a suture passed through tissue and tied around the body of the lead. The leads are secured at the proximal end with a set-screw on the IPG which applies radial pressure to a fixation contact on the distal end of the proximal contacts.

The paddle stimulation leads consist of a combination of implantable materials. Stimulation electrodes at the distal end and electrical contacts at the proximal end are made of a 90-10 platinum-iridium alloy. This alloy is utilized for its bio-compatibility and electrical conductivity. The polymeric body of the lead is polyurethane, which is chosen for its bio-compatibility, flexibility, and high lubricity to decrease friction while being passed through tissue. The polyurethane tubing has a multi-lumen cross section, with one center lumen and eight outer lumens. The center lumen acts as a canal to contain the steering stylet during implantation, while the outer lumens provide electrical and mechanical separation between the wires that carry stimulation from the proximal contacts to distal electrodes. These wires are a bundle of MP35N strands with a 28% silver core. The wires are individually coated with ethylene tetrafluoroethylene (ETFE), to provide an additional non-conductive barrier. At the distal tip of the paddle leads, there is a 2-dimensional array of flat rectangular electrodes, molded into a flat silicone body. Only one side of the rectangular electrodes is exposed, providing the desired uni-directional stimulation. The wires are laser welded to the contacts and electrodes, creating an electrical connection between respective contacts on the proximal and distal ends. Also molded into the distal silicone paddle is a polyester mesh which adds stability to the molded body while improving aesthetics by covering wire routing. The number of individual 8-contact leads used for each paddle is governed by the number of electrodes. Electrodes per paddle range from 8 to 32, which are split into between one and four proximal lead ends. Each proximal lead has 8 contacts (+1 fixation contact). Configurations vary by electrode number, electrode spacing, electrode length, and overall lead length.

Figure 10:
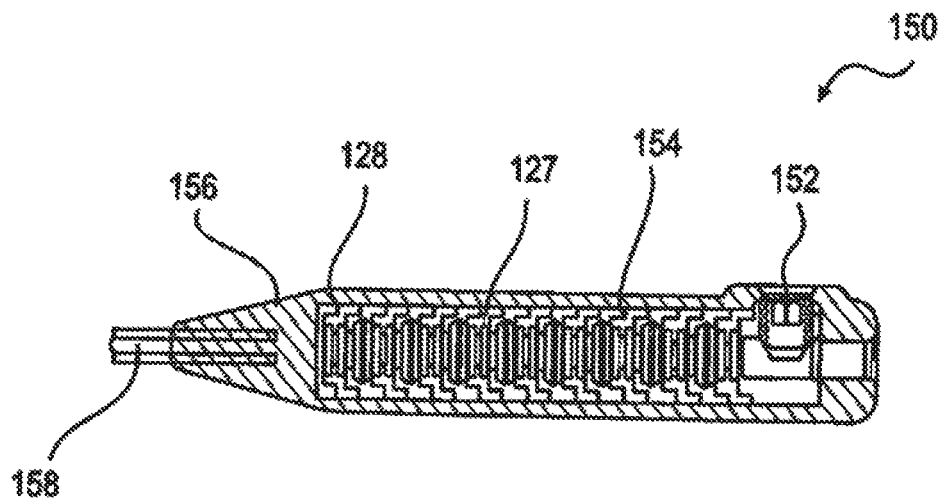
FIG. 10 depicts a lead extension, according to an embodiment.

The lead extensions, as depicted in FIG. 10, are a fully implantable electrical medical accessory to be used in conjunction with the implantable SCS and either percutaneous or paddle leads. The primary function of the lead extension is to increase the overall length of the lead by carrying electrical signals from the IPG to the proximal end of the stimulation lead. This extends the overall range of the lead in cases where the length of the provided leads is insufficient for case. The lead extensions leads must provide a robust, flexible, and bio-compatible electric connection between the IPG and proximal end of the stimulation lead. The extensions may be secured mechanically to the patient using either an anchor or a suture passed through tissue and tied around the body of the extension. Extensions are secured at the proximal end with a set-screw on the IPG which applies radial pressure to a fixation contact on the distal end of the proximal contacts of the extension. The stimulation lead is secured to the extension in a similar fashion, using a set screw inside the molded tip of extension to apply a radial pressure to the fixation contact at the proximal end of the stimulation lead.

The lead extension consists of a combination of implantable materials. At the distal tip of the extension is a 1×8 array of implantable electrical contacts, each consisting of MP35 housing and 90-10 platinum-iridium spring. A silicone seal separates each of the housings. At the proximal end of the contacts is a titanium (6Al4V) cap which acts as a stop for the lead, and at the distal tip, a titanium (6Al4V) block and set screw for lead fixation. The electrical contacts at the proximal end are made of a 90-10 platinum-iridium alloy. This alloy is utilized for its bio-compatibility and electrical conductivity. The polymeric body of the lead is polyurethane, which is chosen for its bio-compatibility, flexibility, and high lubricity to decrease friction while being passed through tissue. The polyurethane tubing has a multi-lumen cross section, with one center lumen and eight outer lumens. The center lumen acts as a canal to contain the steering stylet during implantation, while the outer lumens provide electrical and mechanical separation between the wires that carry stimulation from the proximal contacts to distal electrodes. These wires are a bundle of MP35N strands with a 28% silver core. The wires are individually coated with ethylene tetrafluoroethylene (ETFE), to provide an additional non-conductive barrier. Each lead extension has 8 proximal cylindrical contacts (+1 fixation contact).

Figure 11:
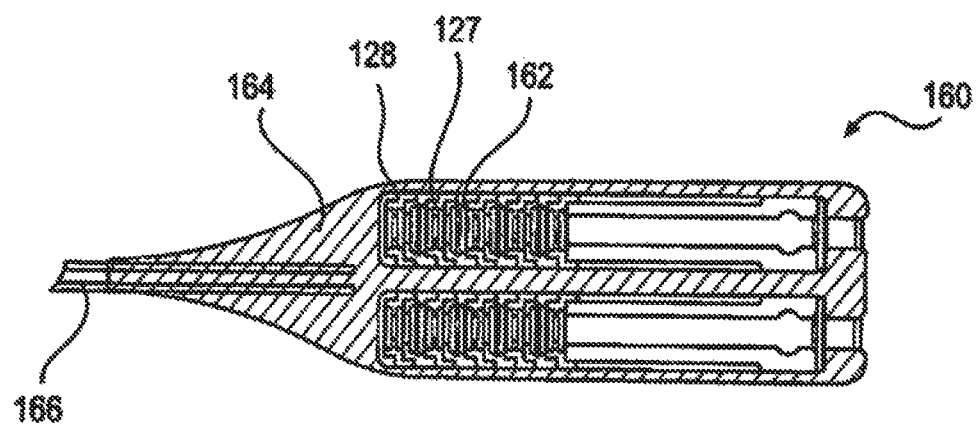
FIG. 11 depicts a lead splitter, according to an embodiment.

The lead splitter, as depicted in FIG. 11, is a fully implantable electrical medical accessory which is used in conjunction with the SCS and typically a pair of 4-contact percutaneous leads. The primary function of the lead splitter is to split a single lead of eight contacts into a pair of 4 contact leads. The splitter carries electrical signals from the IPG to the proximal end of two 4-contact percutaneous stimulation leads. This allows the surgeon access to more stimulation areas by increasing the number of stimulation leads available. The lead splitter must provide a robust, flexible, and bio-compatible electrical connection between the IPG and proximal ends of the stimulation leads. The splitters may be secured mechanically to the patient using either an anchor or a suture passed through tissue and tied around the body of the splitter. Splitters are secured at the proximal end with a set-screw on the IPG which applies radial pressure to a fixation contact on the distal end of the proximal contacts of the splitter. The stimulation leads are secured to the splitter in a similar fashion, using a pair of set screws inside the molded tip of splitter to apply a radial pressure to the fixation contact at the proximal end of each stimulation lead.

The lead splitter consists of a combination of implantable materials. At the distal tip of the splitter is a 2×4 array of implantable electrical contacts, with each contact consisting of MP35 housing and 90-10 platinum-iridium spring. A silicone seal separates each of the housings. At the proximal end of each row of contacts is a titanium (6Al4V) cap which acts as a stop for the lead, and at the distal tip, a titanium (6Al4V) block and set screw for lead fixation. The electrical contacts at the proximal end of the splitter are made of a 90-10 platinum-iridium alloy. This alloy is utilized for its bio-compatibility and electrical conductivity. The polymeric body of the lead is polyurethane, which is chosen for its bio-compatibility, flexibility, and high lubricity to decrease friction while being passed through tissue. The polyurethane tubing has a multi-lumen cross section, with one center lumen and eight outer lumens. The center lumen acts as a canal to contain the steering stylet during implantation, while the outer lumens provide electrical and mechanical separation between the wires that carry stimulation from the proximal contacts to distal electrodes. These wires are a bundle of MP35N strands with a 28% silver core. The wires are individually coated with ethylene tetrafluoroethylene (ETFE), to provide an additional non-conductive barrier. Each lead splitter has 8 proximal contacts (+1 fixation contact), and 2 rows of 4 contacts at the distal end.

Anchors

Figure 12:
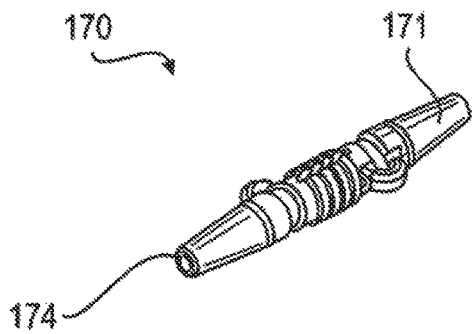
FIG. 12 depicts a sleeve anchor, according to an embodiment.
Figure 13:
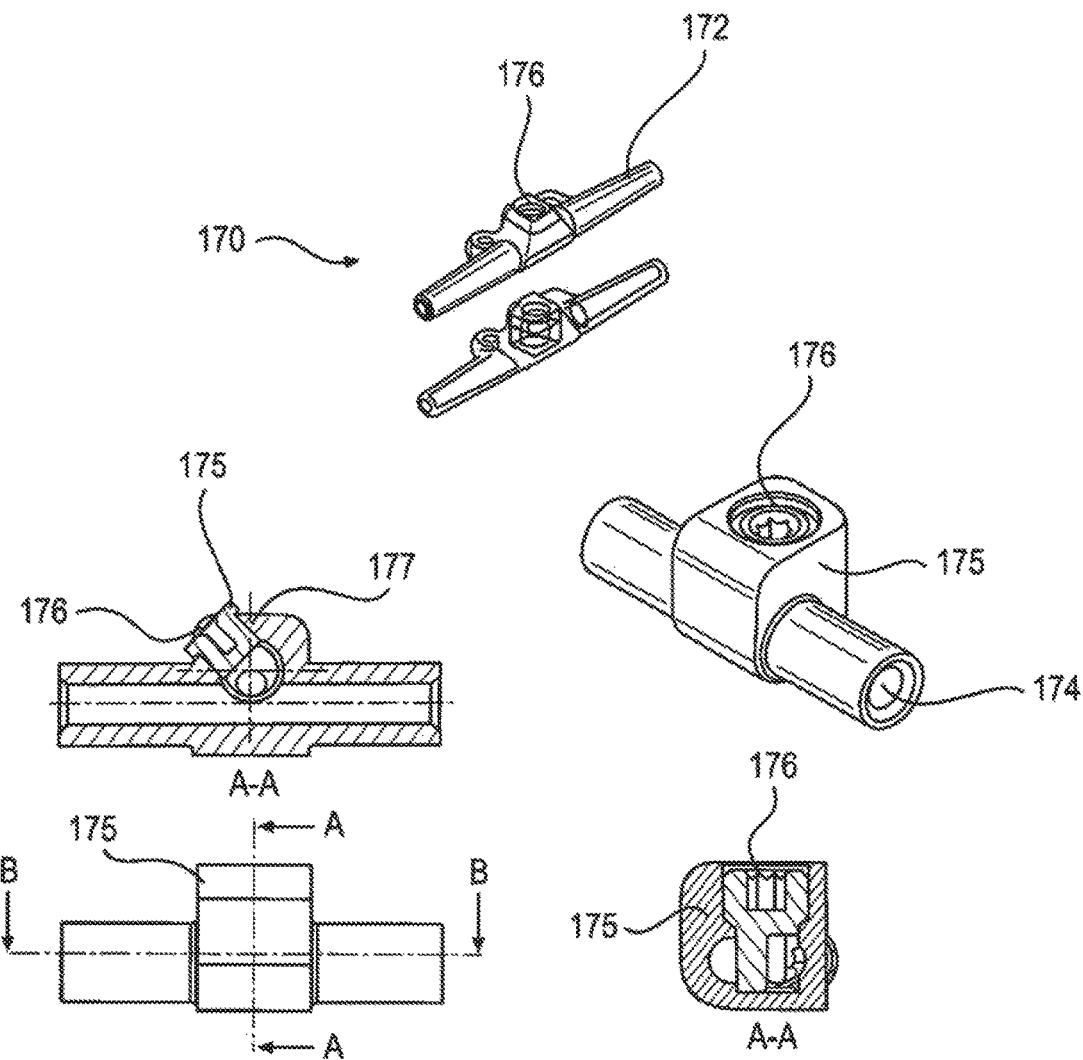
FIG. 13 depicts a mechanical locking anchor, according to an embodiment.

The lead anchor, as depicted in FIGS. 12 and 13, is a fully implantable electrical medical accessory which is used in conjunction with both percutaneous and paddle stimulation leads. The primary function of the lead anchor is to prevent migration of the distal tip of the lead by mechanically locking the lead to the tissue. There are currently two types of anchors, a simple sleeve, depicted in FIG. 12, and a locking mechanism, depicted in FIG. 13, and each has a slightly different interface. For the simple sleeve type anchor, the lead is passed through the center thru-hole of the anchor, and then a suture is passed around the outside of the anchor and tightened to secure the lead within the anchor. The anchor can then be sutured to the fascia. The locking anchor uses a set screw for locking purposes, and a bi-directional disposable torque wrench for locking and unlocking. Tactile and audible feedback is provide for both locking and unlocking.

Both anchors are molded from implant-grade silicone, but the locking anchor uses an internal titanium assembly for locking. The 3-part mechanism is made of a housing, a locking set screw, and a blocking set screw to prevent the locking set screw from back out. All three components are titanium (6A14V). The bi-directional torque wrench has a plastic body and stainless steel hex shaft.

Wireless Dongle

Figure 14:
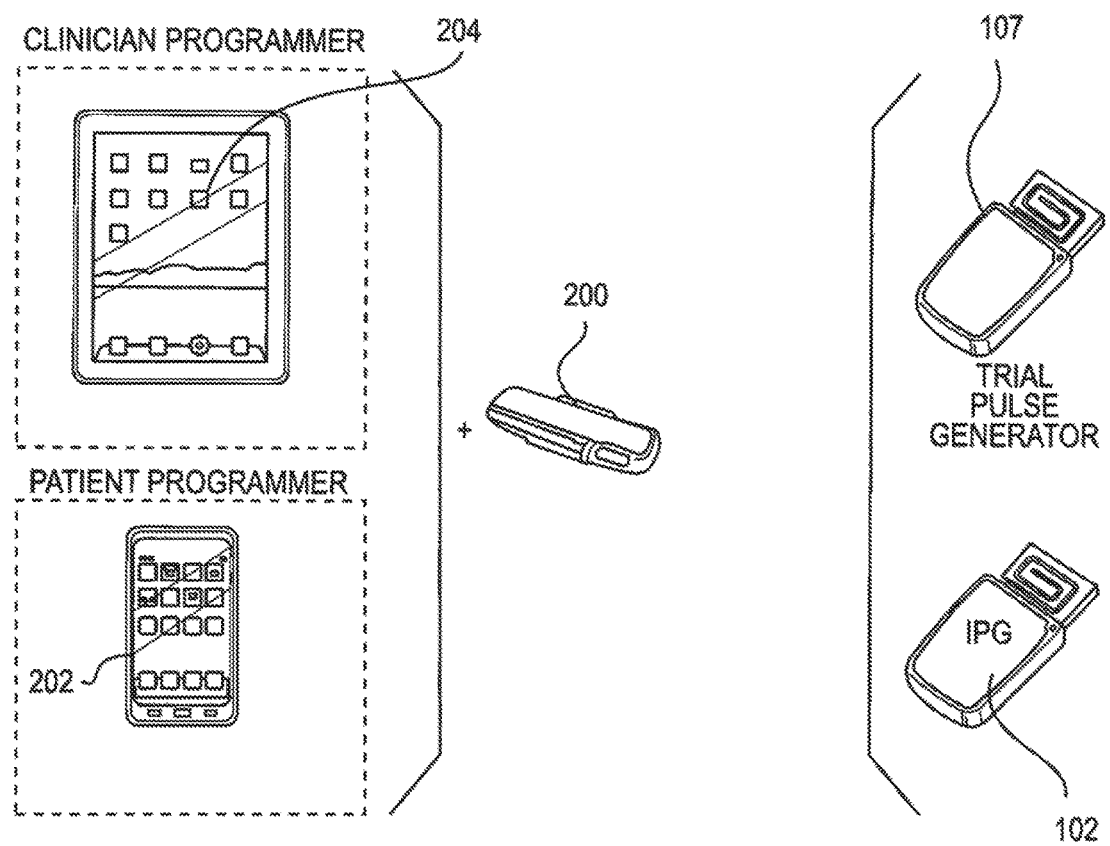
FIG. 14 illustrates communication via a wireless dongle with a tablet/clinician programmer and smartphone/mobile/patient programmer during trial and/or permanent implantation, according to an embodiment.

The wireless dongle is the hardware connection to a smartphone/mobile or tablet that allows communication between the trial generator or IPG and the smartphone/mobile device or tablet, as illustrated in FIG. 14. During the trial or permanent implant phases, the wireless dongle is connected to the tablet through the tablet specific connection pins and the clinician programmer software on the tablet is used to control the stimulation parameters. The commands from the clinician programmer software are transferred to the wireless dongle which is then transferred from the wireless dongle using RF signals to the trial generator or the IPG. Once the parameters on the clinician programmers have been set, the parameters are saved on the tablet and transferred to the patient programmer software on the smartphone/mobile device. The wireless dongle is composed of an antenna, a microcontroller (having the same specifications as the IPG and Trial Generator), and a pin connector to connect with the smartphone/mobile device and the tablet.

Charger

The IPG has a rechargeable Lithium ion battery to power its activities. An external induction type charger is necessary to recharge the included battery inside the IPG wirelessly. The charger consists of a rechargeable battery, a primary coil of wire and a printed circuit board (PCB) for the electronics—all packaged into a housing. When switched on, this charger produces magnetic field and induces voltage into the secondary coil in the implant. The induced voltage is then rectified and then used to charge the battery inside the IPG. To maximize the coupling between the coils, both internal and external coils are combined with capacitors to make them resonate at a particular common frequency. The coil acting as an inductor L forms an LC resonance tank. The charger uses a Class-E amplifier topology to produce the alternating current in the primary coil around the resonant frequency. Below are the charger features;

Charges IPG wirelessly

Charges up to a maximum depth of 30 mm

Integrated alignment sensor helps align the charger with IPG for higher power transfer efficiency Alignment sensor gives an audible and visual feedback to the user Compact and Portable A protected type of cylindrical Li ion battery is used as the charger battery. A Class-E of the topologies of the power amplifiers has been the most preferred type of amplifier for induction chargers, especially for implantable electronic medical devices. It's relatively high theoretical efficiency made it the most favorable choice for devices where high efficiency power transfer is necessary. A 0.1 ohm high wattage resistor is used in series to sense the current through this circuit.

The primary coil L1 is made by 60 turns of Litz wire type 100/44-100 strands of 44 AWG each. The Litz wire solves the problem of skin effect and keeps its impedance low at high frequencies. Inductance of this coil was initially set at 181 uH, but backing it with a Ferrite plate increases the inductance to 229.7 uH. The attached ferrite plate focuses the produced magnetic field towards the direction of the implant. Such a setup helps the secondary coil receive more magnetic fields and aids it to induce higher power.

When the switch is ON, the resonance is at frequency $$f = \frac{1}{2\pi\sqrt{L1C2}}$$

When the switch is OFF, it shifts to $$f = \frac{1}{2\pi\sqrt{L1\frac{C1C2}{C1+C2}}}$$

In a continuous operation the resonance frequency will be in the range $$\frac{1}{2\pi\sqrt{L1C2}} < f < \frac{1}{2\pi\sqrt{L1\frac{C1C2}{C1+C2}}}$$

To make the ON and OFF resonance frequencies closer, a relatively larger value of C1 can be chosen by a simple criteria as follows C1=nC2; a value of n=4 was used in the example above; in most cases 3<n<10.

The voltages in these Class-E amplifiers typically go up to the order of 300 VAC. Capacitors selected must be able to withstand these high voltages, sustain high currents and still maintain low Effective Series Resistance (ESR). Higher ESRs result in unnecessary power losses in the form of heat. The circuit is connected to the battery through an inductor which acts as a choke. The choke helps to smoothen the supply to the circuit. The N Channel MOSFET acts as a switch in this Class-E power amplifier. A FET with low ON resistance and with high drain current Id is desirable.

In summary, the circuit is able to recharge the IPG battery from 0 to 100% in 2 Hr 45 Min with distance between the coils being 29 mm. The primary coil and the Class-E amplifier draws DC current of 0.866 A to achieve this task. To improve the efficiency of the circuit, a feedback closed loop control is implemented to reduce the losses. The loses are minimum when the MOSFET is switched ON and when the voltage on its drain side is close to zero.

The controller takes the outputs from operational amplifiers, checks if they meet the criteria, then it triggers the driver to switch ON the MOSFET for next cycle. The controller needs to use a delay timer, an OR gate and a 555 timer in monostable configuration to condition the signal for driver. When the device is switched ON, the circuit does not start to function right away as there will be no active feedback loop. The feedback becomes active only if the circuit starts to function. To solve this riddle, an initial external trigger is applied to jump start the system.

Alignment Sensor

The efficiency of the power transfer between the external charger and the internal IPG will be maximum only when they are properly aligned. An alignment sensor is absolutely necessary to ensure a proper alignment. This is a part of the external circuit design. The first design is based on the principle called reflected impedance. When the external is brought closer to the internal, the impedance of the both circuits change. The sensing is based on measuring the reflected impedance and test whether it crosses the threshold. A beeper is used to give an audible feedback to the patient; an LED is used for visual feedback.

When the impedance of the circuit changes, the current passing through it also changes. A high power 0.1 ohm resistor is used in the series of the circuit to monitor the change in current. The voltage drop across the resistor is amplified 40 times and then compared to a fixed threshold value using a operational amplifier voltage comparator. The output was fed to a timer chip which in turn activates the beeper and LED to give feedback to the user.

This circuit was successfully implemented in the lab on the table top version. The circuit was able to sense the alignment up to a distance of 30 mm. The current fluctuation in the circuit depends on more factors than reflected impedance alone and the circuit is sensitive to other parameters of the circuit as well. To reduce the sensitivity related to other parameters, one option is to eliminate interference of all the other factors and improve the functionality of the reflected impedance sensor—which is very challenging to implement within the limited space available for circuitry. Another option is to use a dedicated sensor chip to measure the reflected impedance.

A second design uses sensors designed for proximity detector or metal detectors for alignment sensing. Chips designed to detect metal bodies by the effect of Eddy currents on the HF losses of a coil can be used for this application. The TDE0160 is an example of such a chip.

The external charger is designed to work at 75 to 80 kHz, whereas the proximity sensor was designed for 1 MHz. The sensor circuit is designed to be compatible with rest of the external and is fine tuned to detect the internal IPG from a distance of 30 mm.

Programmer

The Clinician Programmer is an application that is installed on a tablet. It is used by the clinician to set the stimulation parameters on the Trial Generator or IPG during trial and permanent implantation in the operating room. The clinician programmer is capable of saving multiple settings for multiple patients and can be used to adjust the stimulation parameters outside of the operations room. It is capable of changing the stimulation parameters though the RF Wireless Dongle when the Trial generator or IPG in the patient is within the RF range. In addition, it is also capable of setting or changing the stimulation parameters on the Trial Generator and/or the IPG through the internet when both the tablet and the Patient Programmers on a smartphone/mobile device both have access to the internet.

The Patient Programmer is an application that is installed on a smartphone/mobile device. It is used by the patient to set the stimulation parameters on the Trial Generator or IPG after trial and permanent implantation outside the operating room. The clinician programmer is capable of saving multiple settings for multiple patients and can be transferred to the Patient Programmer wirelessly when the Clinician Programmer tablet and the Patient Programmer smartphone/mobile device are within wireless range such as Bluetooth from each other. In the scenario where the Clinician Programmer tablet and the Patient Programmer smartphone/mobile device are out of wirelss range from each other, the data can be transferred through the internet where both devices have wireless access such as Wi-Fi. The Patient Programmer is capable of changing the stimulation parameters on the Trial Generator or IPG though the RF Wireless Dongle when the Trial generator or IPG in the patient is within the RF range. However, the Patient Programmer has limitations to changing the stimulation parameters.

Tuohy Needle

Figure 15:
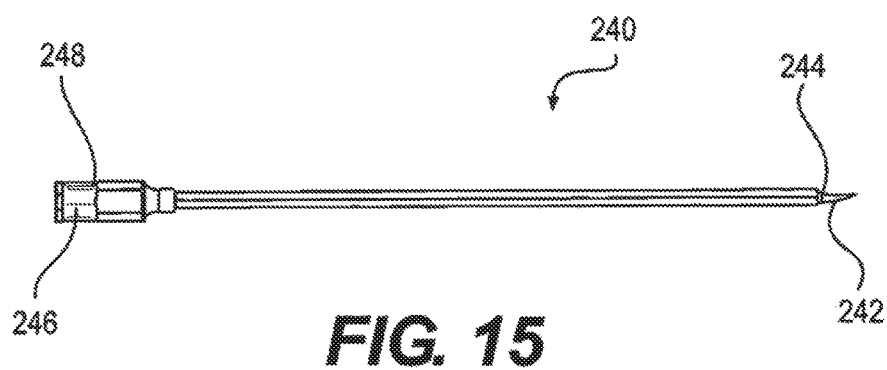
FIG. 15 depicts a Tuohy needle, according to an embodiment.

The tuohy needle, as depicted in FIG. 15, is used in conjunction with a saline-loaded syringe for loss-of-resistance needle placement, and percutaneous stimulation leads, for lead placement into the spinal canal. The tuohy epidural needle is inserted slowly into the spinal canal using a loss-of-resistance technique to gauge needle depth. Once inserted to the appropriate depth, the percutaneous stimulation lead is passed through the needle and into the spinal canal.

The epidural needle is a non-coring 14 G stainless steel spinal needle and will be available in lengths of 5" (127 mm) and 6" (152.4). The distal tip of the needle has a slight curve to direct the stimulation lead into the spinal canal. The proximal end is a standard Leur-Lock connection.

Stylet

Figure 16:
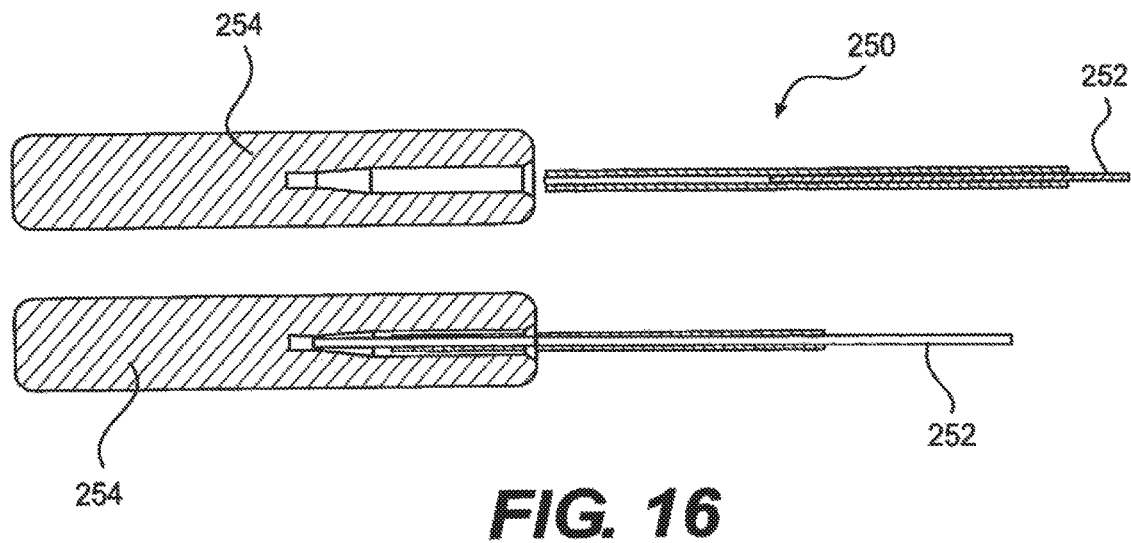
FIG. 16 depicts a stylet, according to an embodiment.

The stylet, as depicted in FIG. 16, is used to drive the tip of a percutaneous stimulation lead to the desired stimulation zone by adding rigidity and steerability. The stylet wire passes through the center lumen of the percutaneous lead and stops at the blocking plug at the distal tip of the lead. The tip of the stylet comes with both straight and curved tips. A small handle is used at the proximal end of the stylet to rotate the stylet within the center lumen to assist with driving. This handle can be removed and reattached allowing anchors to pass over the lead while the stylet is still in place. The stylet wire is a PTFE coated stainless steel wire and the handle is plastic.

Passing Elevator

Figure 17:
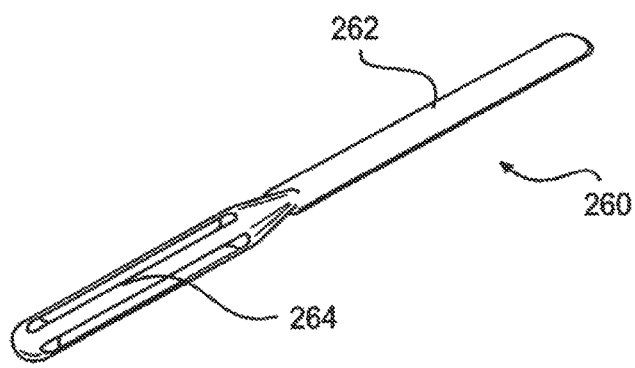
FIG. 17 depicts a passing elevator, according to an embodiment.

The passing elevator, as depicted in FIG. 17, is used prior to paddle lead placement to clear out tissue in the spinal canal and help the surgeon size the lead to the anatomy. The passing elevator provides a flexible paddle-shaped tip to clear the spinal canal of obstructions. The flexible tip is attached to a surgical handle.

The passing elevator is a one-piece disposable plastic instrument made of a flexible high strength material with high lubricity. The flexibility allows the instrument to easily conform to the angle of the spinal canal and the lubricity allows the instrument to easily pass through tissue.

Tunneling Tool

Figure 18:
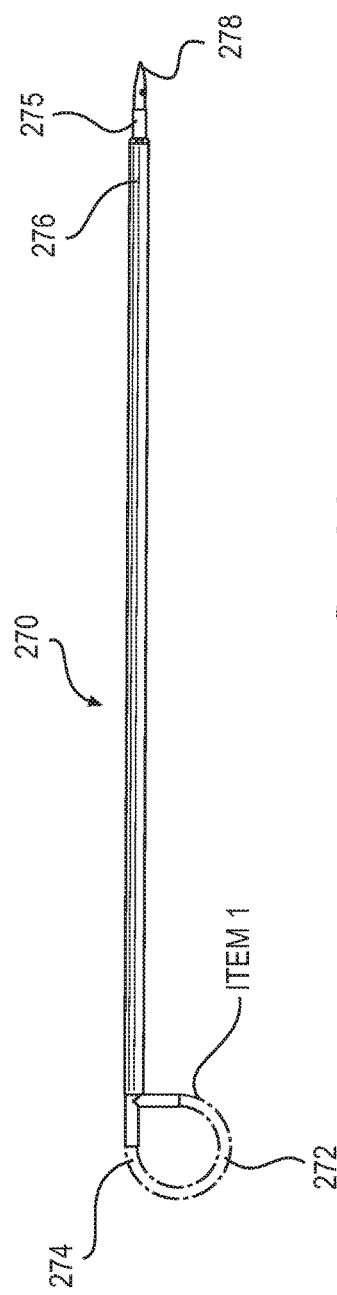
FIG. 18 depicts a tunneling tool, according to an embodiment.

The tunneling tool, as depicted in FIG. 18, is used to provide a subcutaneous canal to pass stimulation leads from the entrance point into the spinal canal to the IPG implantation site. The tunneling tool is a long skewer-shaped tool with a ringlet handle at the proximal end. The tool is cover by a plastic sheath with a tapered tip which allows the tool to easily pass through tissue. Once the IPG implantation zone is bridge to the lead entrance point into the spinal canal, the inner core is removed, leaving the sheath behind. The leads can then be passed through the sheath to the IPG implantation site. The tunneling tool is often bent to assist in steering through the tissue.

The tunneling tool is made of a 304 stainless steel core with a fluorinated ethylene propylene (FEP) sheath. The 304 stainless steel is used for its strength and ductility during bending, and the FEP is used for its strength and lubricity.

Torque Wrench

Figure 19:
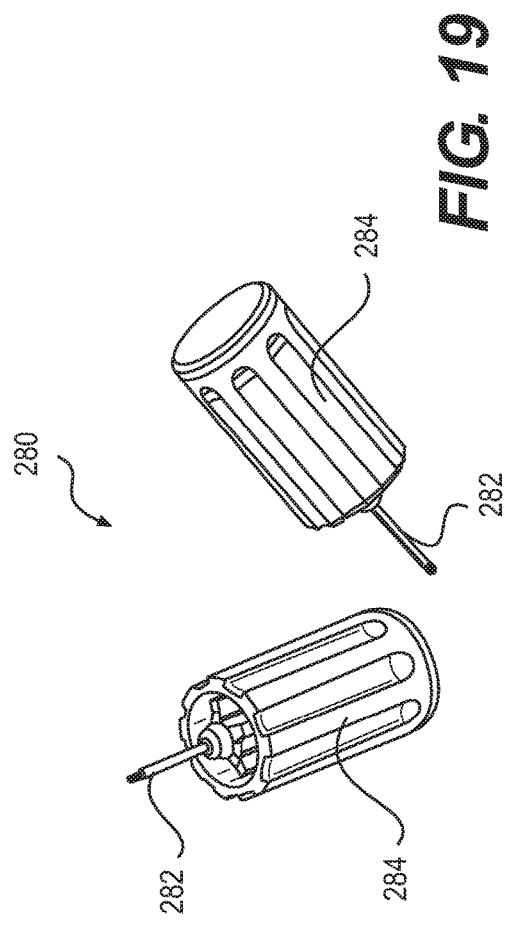
FIG. 19 depicts a torque wrench, according to an embodiment.

The torque wrench, as depicted in FIG. 19, is used in conjunction with the IPG, lead extension and lead splitter to tighten the internal set screw, which provides a radial force against the fixation contact of the stimulation leads, preventing the leads from detaching. The torque wrench is also used to lock and unlock the anchor. The torque wrench is a small, disposable, medical instrument that is used in every SCS case. The torque wrench provides audible and tactile feedback to the surgeon that the lead is secured to the IPG, extension, or splitter, or that the anchor is in the locked or unlocked position.

The torque wrench is a 0.9 mm stainless steel hex shaft assembled with a plastic body. The wrench's torque rating is bi-directional, primarily to provide feedback that the anchor is either locked or unlocked. The torque rating allows firm fixation of the set screws against the stimulation leads without over-tightening.

Trial Patch

The trial patch is used in conjunction with the trialing pulse generator to provide a clean, ergonomic protective cover of the stimulation lead entrance point in the spinal canal. The patch is also intended to cover and contain the trial generator. The patch is a large, adhesive bandage that is applied to the patient post-operatively during the trialing stage. The patch completely covers the leads and generator, and fixates to the patient with anti-microbial adhesive.

The patch is a watertight, 150 mm×250 mm anti-microbial adhesive patch. The watertight patch allows patients to shower during the trialing period, and the anti-microbial adhesive decreases the risk of infection. The patch will be made of polyethylene, silicone, urethane, acrylate, and rayon.

Magnetic Switch

The magnetic switch is a magnet the size of a coin that, when placed near the IPG, can switch it on or off. The direction the magnet is facing the IPG determines if the magnetic switch is switching the IPG on or off.

The invention claimed is:

1. A spinal cord stimulation device for delivering electrical stimulation therapy to a spinal cord, said device comprising:
an implantable pulse generator comprising:
a circuit board housed in a casing, the circuit board including an application specific integrated circuit (ASIC) and a microcontroller, wherein the ASIC is configured to receive digital data from the microcontroller, wherein the ASIC is configured to perform all of the signal processing necessary for electrical stimulation and to generate electrical stimulation pulses based on said signal processing, wherein the ASIC is configured to handle all power management of the implantable pulse generator, and wherein the microcontroller is configured to remain powered down until the ASIC sends a signal to the microcontroller to power up; and
a plurality of electrodes configured to be wired to the implantable pulse generator, wherein the plurality of electrodes are configured to send the electrical stimulation pulses to the spinal cord.

2. The spinal cord stimulation device of claim 1, further comprising one or more leads, wherein the plurality of electrodes are wired to the circuit board via the one or more leads.

3. The spinal cord stimulation device of claim 1 is further configured to be operable at a controlled amplitude at any value within +12.7 mA to −12.7 mA.

4. The spinal cord stimulation device of claim 3, wherein the electrical pulses have a length of between 10 µS to 2000 µS.

5. The spinal cord stimulation device of claim 3, wherein the electrical pulses have a frequency between 0.5 Hz and 1200 Hz.

6. The spinal cord stimulation device of claim 1, wherein the electrical pulses are biphasic.

7. The spinal cord stimulation device of claim 1, wherein the ASIC further comprises a timing generator.

8. The spinal cord stimulation device of claim 1, wherein the ASIC further comprises a power level shifter circuit.

9. The spinal cord stimulation device of claim 1, further comprising a power good (PG) line between the microcontroller and the ASIC.

10. The spinal cord stimulation device of claim 1, further comprising a rechargeable battery housed in the casing to provide power to the ASIC and the microcontroller.

11. The spinal cord stimulation device of claim 10, further comprising a secondary charging coil configured to charge the rechargeable battery disposed in the case.

12. The spinal cord stimulation device of claim 11, wherein the secondary charging coil is an induction coil.

13. The spinal cord stimulation device of claim 1, wherein the implantable pulse generator further comprises an RF radio antenna which allows the implantable pulse generator to send commands associated with programming the signals for electrical stimulation.

14. A spinal cord stimulation device for delivering electrical stimulation therapy to a spinal cord, said device comprising:
an implantable pulse generator comprising:
a circuit board housed in a casing, the circuit board including an application specific integrated circuit (ASIC) and a microcontroller, wherein the ASIC is configured to perform all of the signal processing necessary for electrical stimulation and to generate electrical stimulation pulses based on said signal processing, wherein the ASIC is configured to handle all power management of the implantable pulse generator, and wherein the microcontroller is configured to remain powered down until the ASIC sends a signal to the microcontroller to power up;
a plurality of electrodes configured to be wired to the implantable pulse generator, wherein the plurality of electrodes are configured to send the electrical stimulation pulses; and
one or more leads, wherein the plurality of electrodes are wired to the circuit board via the one or more leads.

15. The spinal cord stimulation device of claim 14 is further configured to be operable at a controlled amplitude at any value within +12.7 mA to −12.7 mA.

16. The spinal cord stimulation device of claim 15, wherein the ASIC is further configured to generate the electrical pulses which have a length of between 10 µS to 2000 µS.

17. The spinal cord stimulation device of claim 15, wherein the ASIC is further configured to generate the electrical pulses which have a frequency between 0.5 Hz and 1200 Hz.

18. The spinal cord stimulation device of claim 14, wherein the ASIC is further configured to generate the electrical pulses which are biphasic.

19. The spinal cord stimulation device of claim 14, wherein the ASIC further comprises a timing generator.

20. The spinal cord stimulation device of claim 14, wherein the ASIC further comprises a power level shifter circuit.

* * * * *